United States Patent [19]

Thurston et al.

[11] Patent Number: 5,732,704
[45] Date of Patent: Mar. 31, 1998

[54] RADIATION BASED METHOD LOCATING AND DIFFERENTIATING SENTINEL NODES

[75] Inventors: Marlin O. Thurston, Columbus; Karl W. Olson, Worthington; Richard C. Orahood, Delaware; Michael D. Magill, Columbus, all of Ohio

[73] Assignee: Neoprobe Corporation, Dublin, Ohio

[21] Appl. No.: 542,955

[22] Filed: Oct. 13, 1995

[51] Int. Cl.$^6$ ............................... A61B 6/00; G01T 1/161
[52] U.S. Cl. ...................... 128/659; 128/654; 250/336.1
[58] Field of Search ................... 128/659, 653.1, 128/654, 898; 250/336.1, 370.07; 607/901

[56] References Cited

U.S. PATENT DOCUMENTS

| | | | |
|---|---|---|---|
| 4,782,840 | 11/1988 | Martin, Jr. et al. | 128/654 |
| 4,801,803 | 1/1989 | Denen et al. | 250/336.1 |
| 4,889,991 | 12/1989 | Ramsey et al. | 250/336.1 |
| 5,070,878 | 12/1991 | Denen | 128/659 |
| 5,101,827 | 4/1992 | Goldenberg | 128/653.4 |
| 5,151,598 | 9/1992 | Denen | 250/336.1 |
| 5,170,055 | 12/1992 | Carroll et al. | 250/336.1 |
| 5,209,919 | 5/1993 | Turteltaub et al. | 424/1.1 |
| 5,383,456 | 1/1995 | Arnold et al. | 128/653.1 |
| 5,427,766 | 6/1995 | Dowd | 424/1.45 |
| 5,441,050 | 8/1995 | Thurston et al. | 128/659 |
| 5,475,219 | 12/1995 | Olson . | |
| 5,520,182 | 5/1996 | Leighton et al. | 128/654 |
| 5,579,766 | 12/1996 | Gray | 128/653.1 |
| 5,582,172 | 12/1996 | Papisov et al. | 128/653.4 |
| 5,590,656 | 1/1997 | O'Dorisio et al. | 128/654 |

OTHER PUBLICATIONS

Gamma–Probe Guided Lynph Node Localization in Malignant Melanoma Alex et al. Surgical Oncology 19932:303–308.

Gamma probe Guided Localizationof Lymph Nodes Alex et al. Surgical Oncology 1993:2:137–143.

Surgical resection and radidocalization of the sentinel lymph node in breast cancer using a gamma probe Krag, et al. Surgical Oncology 1993: 2:335–340.

Lymphatic Mapping and Sentinel Lymphaderectomy for Breast Cancer Guilano, et al. Anals of Surgery vol. 220 No. 3, pp. 391–401.

Lymphoscintigraphy in High Risk Melanoma of the Trunk Uren, et al. Lymphoscintigraphy/Melanoma Channels, Sentinel/Nodes.

J. Nucl. Med. vol. 34, No. 9, Sep. 1993 Technical Details of Intraoperative Lymphatic Mapping Arch Surg. vol. 127, Apr. 1992.

*Primary Examiner*—Marvin M. Lateef
*Assistant Examiner*—Shawna J. Shaw
*Attorney, Agent, or Firm*—Mueller and Smith, LPA

[57] ABSTRACT

The method for identifying a sentinel lymph node located within a grouping of regional nodes at a lymph draininage basin associated with neoplastic tissue wherein a radiopharmaceutical is injected at the situs of the neoplastic tissue. This radiopharmaceutical migrates along a lymph duct toward the drainage basin containing the sentinel node. A hand-held probe with a forwardly disposed radiation detector crystal is maneuvered along the duct while the clinician observes a graphical readout of count rate amplitudes to determine when the probe is aligned with the duct. The region containing the sentinel node is identified when the count rate at the probe substantially increases. Following incision, the probe is maneuvered utilizing a sound output in connection with actuation of the probe to establish increasing count rate thresholds followed by incremental movements until the threshold is not reached and no sound cue is given the surgeon. At this point of the maneuvering of the probe its detector will be in adjacency with the sentinel node which then may be removed.

18 Claims, 18 Drawing Sheets

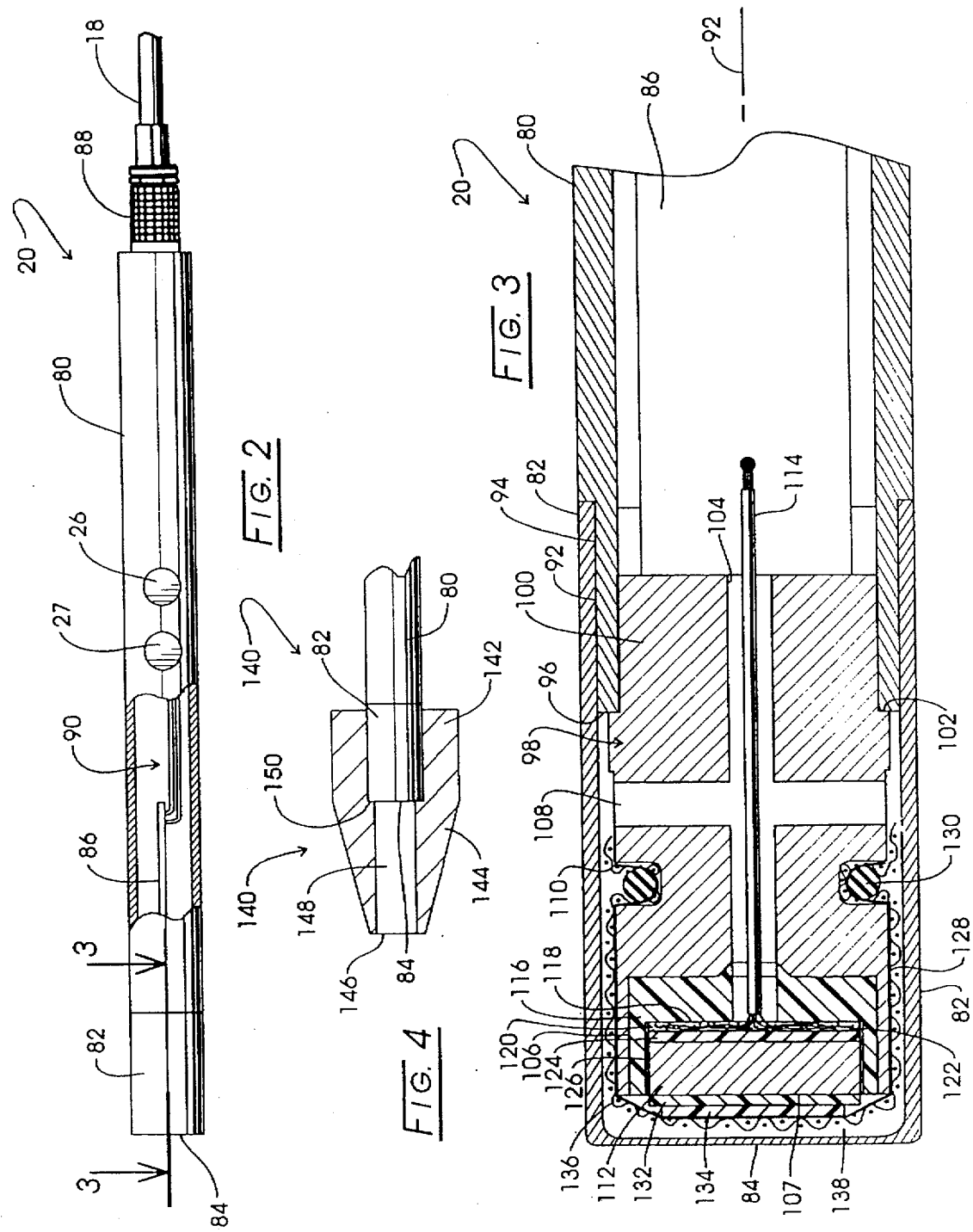

RADIATION BASED METHOD LOCATING AND DIFFERENTIATING SENTINEL NODES

BACKGROUND OF THE INVENTION

An evaluation of the presence or absence of tumor metastasis or invasion has been a major determinant for the achievement of an effective treatment for cancer patients. Studies have determined that about 30% of patients with essentially newly-diagnosed minor will exhibit clinically detectable metastasis. Of the remaining 70% of such patients who are deemed "clinically free" of metastasis, about one-half are curable by local tumor therapy alone. See Sugarbaker, E. V., "Patterns of Metastasis in Human Malignancies", *Cancer Biol. Rev.* 1981 2:235. The remaining patients will have clinically occult (undetected) micrometastasis that ultimately become manifest.

The involvement of the lymph system in tumor metastasis has been the subject of extensive investigation and is well established. Lymphatic systems are present as widely dispersed tissues, fluids, and cells concerned in a variety of interrelated functions of the mammalian body including the circulation and modification of tissue fluid formed in the capillary beds, and the removal by mononuclear phagocytes of cell debris and foreign matter. The lymphatic system is importantly involved in participation with the blood vascular system in developing the immune response of the lymphocytes and other cells. Lymph flows within the system as a consequence of a variety of perceived mechanisms of organ and tissue dynamics. For certain cancers, metastasis occurring in consequence of lymph drainage will result in an initial location or positioning of neoplastic cells at certain lymph nodes typically deemed "regional nodes" within a pertinent lymph drainage basin. Some cancers, for example, melanomas, have been observed to exhibit variability in lymphatic drainage patterns emanating from different portions of the body. Other cancers, such as those encountered in the breast will evidence somewhat more predictable nodal involvement. In designing forms of cancer disease management, therefore, efforts are directed to the identification of affected lymph nodes. For melanomas, it has been a more recent practice to identify the pertinent drainage basin or regional nodes along with an evaluation of the extent of lymph involvement with micrometastasis. A pre-surgical step undertaken in about 20% of investigational procedures concerning melanomas looks to carrying out of a gamma camera generated form of lymphoscintigaphy which gives the clinician a gross two-dimensionally limited image, generally showing the tumor site injection of sulfur colloid labeled with technetium 99-m ($^{99m}T_c$) and, spaced therefrom, a region of radioactivity at the pertinent regional lymph nodes. The latter information at least confirms the path of drainage and the location of the proper drainage basin. Regional nodes then are removed and submitted for pathology evaluation.

For cancers such as breast cancer, the sites of lymph node involvement are commonly encountered at axillary, internal mammary, and supraclavicular lymph node regions. Of these, the axillary lymph node region is the principal site of regional metastasis from carcinoma of the breast, and approximately 40% of patients have evidence of spread to the axillary nodes. In early approaches to the disease, these axillary nodes were removed as a form of therapy. Presently, however, their positive involvement, or lack thereof, has become the subject of diagnostics as opposed to therapy. In this regard, the combination of the presence and extent of metastasis to the axilla represents the single most important prognostic factor for the management of patients with breast cancer. See generally "Cancer, Principles and Practice of Oncology", vol. 1, 4th ed. DeVita, Jr., et al., chapter 40, Harris, et al., J.P. Lippincott Co., Philadelphia, Pa. (1993).

The axilla is a triangular region bounded by the axillary vein superiorly, the *latissimus dorsi* laterally, and the *serratus* anterior medially. With more current diagnostic procedures, essentially all axillary nodes at the axilla assumed to represent the drainage basin are removed during surgery for analysis. In general, somewhere between 10 and 30 nodes will be removed in the course of dissection with, of course, the attendant risks. In this regard, these nodes are generally surrounded by investment or fatty tissue and visualization of them necessarily is limited. Such dissection will pose risks of cutting the long thoracic nerve, the thoracic-dorsal nerve, the nerve to the *pectoralis major* or the axillary vein. Morbidity may occur in some cases due to regional node removal and patients are known to frequently discuss a numbing of the arm region following the procedure.

While this form of somewhat radical axillary lymph node dissection has been the conventional approach to determining nodal metastatic involvement, more recent data suggests that less radical axillary node evaluation procedures may generate equivalent information for staging and patient management, but with far more limited dissection and resultant trauma, as discussed below.

Patient management for staging purposes for the case of cutaneous melanoma is highly predicated upon determinations of lymph involvement. A number of factors are involved in the prognosis of the disease, including, inter alia, location, tumor thickness, level of invasion, growth patterns, and of particular importance the identification of regional node metastatic involvement. Generally, surgical excision of metastatic nodes within the drainage basin of a lesion has been considered the only effective treatment for cure or disease control. Some investigators have preferred to excise only clinically demonstrable metastatic nodes associated with the lesion, while others have chosen to excise the nodes even where they may appear normal because of the risk of the presence of occult (clinically undetectable) metastasis. A substantial dialog has been carried on by investigators as to whether or not elective lymph node dissection or lymphadenectomy is an appropriate therapy. Elective lymphodenectomy has the major advantage of treating a nodal metastasis at a relatively early stage in its natural history when the tumor burden is low. On the other hand, such an approach may subject patients to surgery which would otherwise have been unnecessary. In particular, where patients exhibit a clinical Stage I level of the disease, there will be no nodal metastasis present and no benefit then can be realized from regional lymphadenectomy.

Relatively recently, Morton, et al., undertook an investigation of a procedure designed to identify that lymph node nearest the site of a melanoma and within the pertinent lymph drainage basin. Such a node, being on the most direct drainage pathway will present the most likely site of early metastasis and is referred to as the "sentinel node". Thus, by carrying out only a limited dissection specific to this node and performing pathologic analysis of it, staging can be achieved without at least initial resort to more radical lymphadenectomy. With the approach, once the drainage basin from a lesion is identified, for example, by lymphoscintigraphy, an intraoperative mapping of the cutaneous lymphatics with vital dye is carried out at the time of surgical removal of the primary lesion. The vital dye, for example of blue color, is injected at the site of the lesion and tracked by blunt dissection until the sentinel node is reached. That node is now exclusively of blue color and readily identified. Thus, the sentinel draining lymph node of each primary melanoma is isolated and removed. By examining the sentinel nodes, for example by frozen section using routine hematoxylin-eosin histopathological techniques, as well as rapid immunohistochemical techniques, only those patients who have evidence of micrometastasis in the sentinel draining node are subject to subsequent lymphodenectomy. See generally, Morton D., Wen D-R, Wong J., et al. "Technical Details of Intraoperative Lymphatic Mapping for Early Stage Melanoma", Arch. Surg. 1992: 127:392–399; and "Lymphoscintigraphy in High-Risk Melanoma of the Trunk: Predicting Draining Node Groups, Defining Lymphatic Channels and Locating the Sentinel Node", R. F. Uren, et. al, J. Nucl Med 1993; 34:1435–1440.

The approach of Morton, et al., also has been undertaken to moderate the otherwise somewhat radical axillary lymph node dissection common in staging breast cancer. Through the utilization of the noted vital dyes in conjunction with the lymph drainage system from primary breast minor, less radical sentinel node based procedures may result in adequate axillary staging and regional control. With the procedure, in general, a vital blue dye is injected into the breast mass and surrounding breast parenchyma. Following a relatively short interval, a transverse incision is made just below the hair bearing region of the axilla. Blunt dissection is performed until a lymphatic tract or duct leading to a blue stained node is identified. The lymph duct, having a blue color, provides a guide path leading to the location of the most proximal lymph node and thus the sentinel node. This sentinel node is excised and evaluated. While the procedure calls for considerable surgical experience and talent associated with the delicate task of following the blue duct (a raptured dye-carrying duct can be problematic), the ability to identify a tumor-free sentinel lymph node will enable the surgeon to accurately stage metastasis-free breast cancer patients without subjecting them to the risks of radical dissection. The approach may also improve histologic staging by enabling the pathologist to focus on fewer lymph nodes. See generally Guiliano, A. E.; Kirgan, B. M.; Guenther, J. M.; and Morton, D. L., "Lymphatic Mapping and Sentinel Lymphadenectomy for Breast Cancer", *Annals of Surgery*, vol. 220, no. 3: 391–401, 1994, J.B. Lippincott Company.

Lymph node involvement in metastasis also has been the subject of investigation in other quite different forms of cancer such as colonic cancer. This has been through the utilization of a hand-held radiation responsive probe. U.S. Pat. No. 4,782,840 by Martin., M.D. and Thurston, Ph.D., entitled "Method for Locating, Differentiating, and Removing Neoplasms", issued Nov. 8, 1988, reviews the approaches of nuclear medicine for locating colonic tumor. The patent discloses a method for locating, differentiating, and removing neoplasms which utilizes a radiolabelled antibody in conjunction with the radiation detection probe, which the surgeon may use intraoperatively in order to detect the sites of radioactivity. Because of the proximity of the detection probe to the labelled antibody, the faint radiation emanating from occult sites becomes detectable because, in part, of the inherent application of the approximate inverse square law of radiation propagation. The procedure is known as the RIGS® procedure, RIGS being a registered trademark of Neoprobe Corporation, Dublin, Ohio. The RIGS system has been found to provide a unique identification of involved lymph nodes for staging evaluation. See, for example, Nieroda, C. A., et al., Surg. Gynecol. Obstet. vol. 169(1), 1989, pp 35–40. This RIGS lymph evaluation also may be employed with certain more minimally invasive procedures as described by M. W. Arnold, M.D., and M. O. Thurston, Ph.D., in U.S. Pat. No. 5,383, 456, entitled "Radiation-Based Laparoscopic Method for Determining Treatment Modality" issued Jan. 24, 1995.

As an aspect of the RIGS system, the location of involved lymph material or neoplasm is carried out utilizing a statistical approach. With this approach, a background count rate of radiation emanation is developed, for example, at the aorta of the patient for an interval of time, for example, 5 seconds. A microprocessor-based control system then calculates a statistically significant value, for example a predetermined number of standard deviations of the basic count rate to derive a statistically significant threshold radiation count rate level. The ranging procedure is referred to by surgeons as "squelching". Operating in conjunction with that threshold level, the instrument provides the surgeon with audible cues representing that a high probability of tumor involvement is present at a location closely adjacent the forward window of the hand-held probe.

SUMMARY

The present invention is addressed to an improved method for identifying a sentinel lymph node associated, for example, with melanomas or breast tumor wherein a radiopharmaceutical is injected at the site of the neoplastic tissue and is permitted to migrate along a lymph duct to collect at a sentinel node. A hand-held radiation probe initially is employed in conjunction with a graphics readout to locate that lymph duct or ducts within which the injected radiopharmaceutical has migrated. This radiopharmaceutical containing lymph duct then may be tracked or surveyed by moving the probe along the epidermis of the patient while maintaining the forward detector containing portion of the probe in parallel relationship with the surface being scanned. The probe is moved in a somewhat undulating or crossing fashion while the clinician observes a graphics readout at a monitor or the like, the location of the duct being identified by the relative location of the probe when the graphics readout shows a peak in count rate amplitude. Preferably, a circularly accessed data memory is utilized in conjunction with a graphics display. A visual perception of amplitude peaks is developed notwithstanding the highly random nature of radiation emission. Such tracking along the lymph duct is practical by virtue of a determination and proof that radiation within that small vessel attenuates not according to the inverse square law of radiation propagation, but as a first power. As the probe locates the regional node containing drainage basin, the count rates will increase substantially and the sentinel node is then differentiated by utilizing either the squelching feature or a manual threshold adjusting feature of the hand-held probe in a three-dimensional guidance based manner. This guidance procedure now is aided by the nature of photon emission from the situs of the sentinel lymph node. The approximate inverse square law of radiation propagation now applies with respect to the node as the surgeon utilizes count rate threshold value adjusted in a reiterating manner as the forward detector surface of the probe progresses toward the sentinel node. The noted threshold adjusting or squelching procedures are ones wherein the aural perceptive aspect of the probe is employed as opposed to the visual aspects heretofore used in locating the drainage basin. Thus, the surgeon, now working through an incision over the sentinel node, is permitted to visually concentrate on the subject of sentinel node identification. The or threshold alignment squelching procedures are ones wherein a higher count rate threshold is established for the probe as a condition precedent to the generation of an aural signal or siren form of sound. Thus, as the forward surface of the probe is moved inwardly toward the sentinel node, the approximate inverse square law of propagation applies with respect to the count rates and the probe count rate threshold values are increased successively as it is moved and that movement will be toward peak counting rates. When a squelch actuation of the probe subsequently accompanied by only slight movement evokes as on and off states of the aural output, then the forward surface of the probe is directed toward and axially oriented at the sentinel node which then may be excised. Thus, the sentinel node is located and removed with minimal trauma to the patient.

As another aspect, the invention provides a method for identifying a sentinel lymph node located within a grouping of regional nodes at a lymph drainage basin associated with neoplastic tissue which comprises the steps of:

(a) identifying the situs of the neoplastic tissue;

(b) injecting at the situs of the neoplastic tissue a radiopharmaceutical effective for movement with lymph along a lymph duct;

(c) providing a hand manipulable radiation probe with a detector having a forward surface which is perpendicular to a detector axis, the probe being responsive to photon emissions impinging at the forward surface of the detector to provide probe output signals;

(d) providing a control system for receiving the probe output signals, this control system providing an energy level validation of the pulse output signals and a perceptible output representing a photon count rate of value above a threshold count rate value this threshold count value being derived in conjunction with a base count rate established by the probe output signals in response to photon emissions from the radiopharmaceutical subsequent to its aforesaid injection, the system being actuable to increase the threshold count rate value;

(e) permitting the radiopharmaceutical to migrate along a lymphatic duct to the situs of the sentinel lymph node following the injection;

(f) positioning the probe detector forward surface at an initial position at the anticipated region of the situs of the sentinel lymph node and actuating the control system;

(g) then moving the probe a distance to a next position, and in the presence of a generation of the perceptible output, actuating the control system so as to elevate the threshold count rate value; and (h) reiterating step (g) until the movement deriving the perceptible output is of a distance of short extent effective to identify a position of the probe corresponding with a peak rate of the photon emissions impinging at the forward surface of the detector and representing an alignment of the detector axis with the sentinel lymph node.

Another feature of the invention provides a method for identifying a sentinel lymph node located within a grouping of regional nodes at a lymph drainage basin of a patient which is associated with neoplastic tissue, comprising the steps of:

(a) identifying the situs of the neoplastic tissue;

(b) injecting through the epidermis of the patient, at the situs of the neoplastic tissue, a radiopharmaceutical effective for movement with lymph along a lymph duct;

(c) providing a hand manipulable radiation probe with a detector having a forward surface which is perpendicular to a detector axis, the probe being responsive to photon emissions impinging at the forward surface of the detector to provide probe output signals;

(d) providing a control system for receiving the probe output signals, the control system generating a first visually perceptible graphics output representing a photon count rate corresponding with the probe output signals;

(e) permitting the radiopharmaceutical to migrate along a lymphatic duct toward the situs of the sentinel lymph node following the injection;

(f) orienting the probe detector forward surface in a manner defining a scanning surface at a location adjacent the epidermis and within a region adjacent the situs of neoplastic tissue;

(g) surveying the region of the lymphatic duct with respect to the epidermis by:

(1) moving the probe outwardly and transversely with respect to the situs of the neoplastic tissue while maintaining the detector forward surface in parallel relationship with the scanning surface;

(2) simultaneously determining peak photon count rates from the control system first perceptible output;

(3) designating the position of the probe detector axis at the epidermis as extending into adjacency with a portion of the lymphatic duct for each determined peak photon count;

(4) reiterating steps (1), (2), and (3) until the first perceptible output represents an enhanced photon count rate corresponding with a lymph node contained concentration of the radiopharmaceutical; and (h) locating and isolating the lymph node within the region from which enhanced photon count rate emanates.

Still another feature of the invention provides a method for identifying a sentinel lymph node within a patient, the sentinel lymph node being located within a grouping of regional nodes at a lymph drainage basin associated with neoplastic tissue, comprising the steps of:

(a) identifying the situs of the neoplastic tissue;

(b) injecting at the situs of the neoplastic tissue a radiopharmaceutical effective for movement with lymph along a lymph duct;

(c) providing a hand manipulable radiation probe with a detector adjacent a window, the detector having a forward surface which is perpendicular to a detector axis and the probe being responsive to photon emissions impinging at the forward surface of the detector to provide probe output signals;

(d) providing a control system for receiving the probe output signals, the control system providing a perceptible output representing a photon count rate of value above a threshold count rate derived in conjunction with a base count rate established by the probe output signals in response to photon emissions from the radiopharmaceutical occurring subsequent to the injection thereof and being actuable to increase the threshold count rate value;

(e) permitting the radiopharmaceutical to migrate along a lymphatic duct to the situs of the sentinel lymph node following the injection;

(f) positioning the probe detector forward surface at an initial position at the anticipated region of the situs of the sentinel lymph node and actuating the control system;

(g) then moving the probe transversely along the epidermis of the patient a distance to a next position, and in the presence of a generation of the perceptible output, actuating the control system so as to elevate the threshold count rate value;

(h) reiterating step (g) until movement deriving the perceptible output is a distance of short extent effective to identify, indicating a first position of the probe corresponding with a peak rate of photon emissions impinging at the forward surface of the detector and representing an alignment of the detector axis with the sentinel lymph node;

(i) forming a surgical opening in the patient at the first position;

(j) then moving the probe window inwardly within the opening to a next position and in the presence of a generation of the next perceptible output, actuating the control system so as to effect a termination of the perceptible output; and (k) reiterating step (j) until the perceptible output is not derived, indicating a second position of the probe corresponding with a peak rate of the photon emissions impinging at the forward surface of the detector and representing an adjacency of the probe window with the sentinel node.

Other objects of the invention will, in part, be obvious and will, in part, appear hereinafter. The invention, accordingly, comprises the method possessing the steps which are exemplified in the following detailed disclosure.

For a fuller understanding of the nature and objects of the invention, reference should be had to the following detailed description taken in connection with the accompanying drawings.

BRIEF DESCRIPTION OF THE DRAWINGS

FIG. 2 is a side view of a radiation probe employed with the system of FIG. 1 with portions broken away to reveal internal structure;

FIG. 3 is a sectional view taken through the plane 3—3 in FIG. 2;

FIG. 4 is a partial side view showing a collimator employed with the probe of FIG. 2 with portions broken away to reveal internal structure;

DETAILED DESCRIPTION OF THE INVENTION

Figure 1:
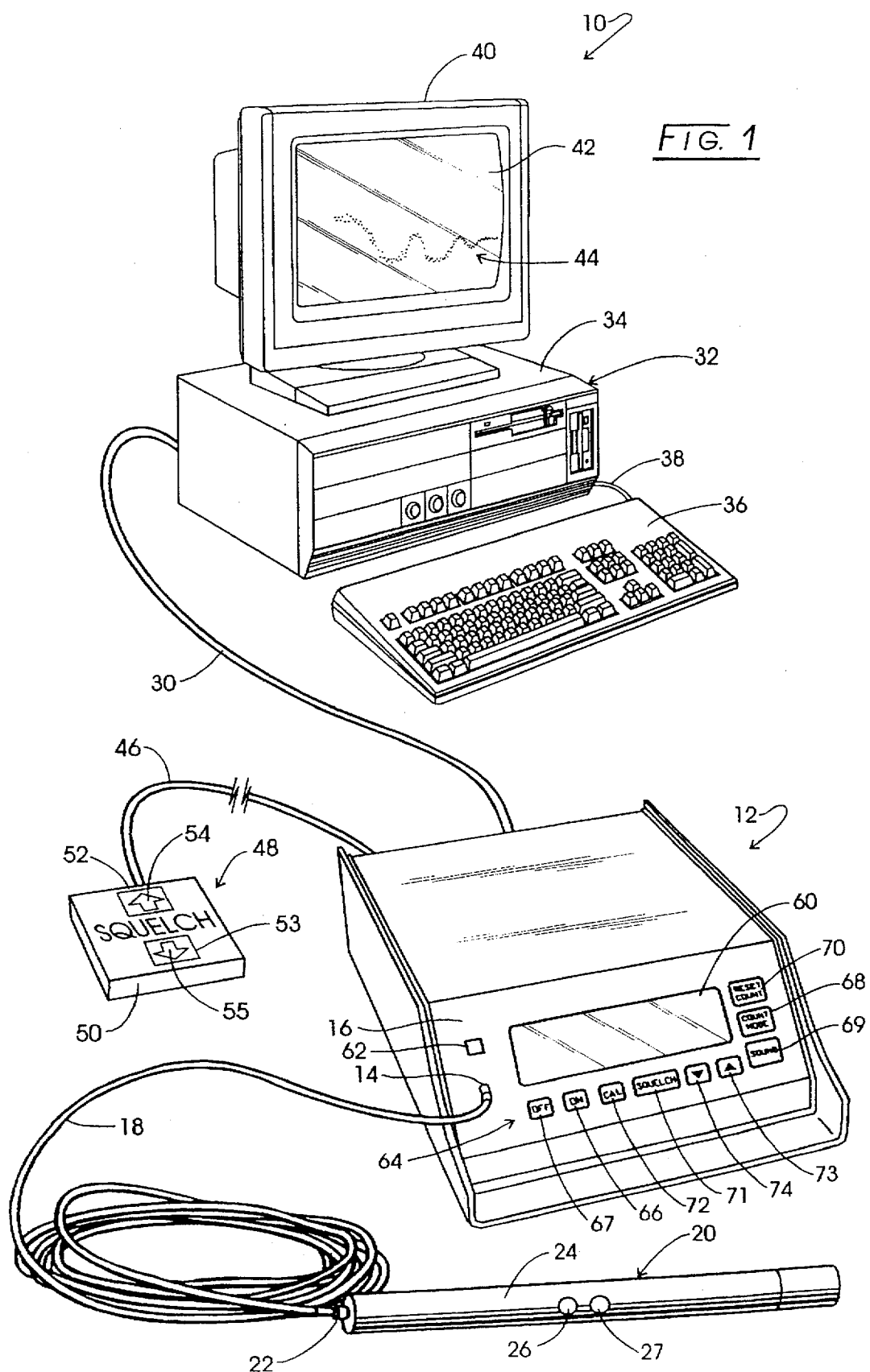
FIG. 1 is a pictorial representation of the system and instrumentation employed with the method of the invention.

The present invention, in effect, has two aspects. One of these aspects is concerned with mapping or surveying a lymph vessel which drains from the site of a neoplasm such as a melanoma or breast tumor to a sentinel lymph node. Another aspect involves the detection and isolation of that node once its regional position is located. In general, the phenomenon associated with radiation propagation or photon emission is somewhat different when considering radiation emanating from a lymph duct as opposed to radiation emanating from a small source such as a lymph node. A lymph duct will be seen to approximate a line source producing a characteristic $R^{-1}$ function. A lymph node, to the extent that it represents a point source, produces the characteristic $R^{-2}$ function. Equipment which is utilized in carrying out the diagnostic modality preferably is an adaptation of the equipment heretofore employed with the radioimmuno-guided surgical system (RIGS) or procedure used in the location of tumor sites, for example, in the colonic region. The RIGS procedure typically is employed with a radiolabelled locator which specifically binds a marker produced or associated with neoplastic tissue. Such locators include substances which preferentially concentrate at tumor sites by binding with a marker (the cancer cell or product of the cancer, for example) produced by or associated with neoplastic tissue or neoplasms. Because the locater is injected into the bloodstream of the patient, equipment used with the RIGS procedure necessarily must work with radiation background levels and low radionuclide concentrations at tumor sites. For the present procedure, however, such locaters are not employed, a radiopharmaceutical being utilized in conjunction with a carrier. For example, a sulfur colloid labeled with $^{99m}$Tc may be used, it being of relatively low cost, readily available, and representing an approved pharmaceutical product. Another advantage associated with its use resides in its short halflife (6 hours) which results in its being essentially gone from the body of a patient in about three days following injection. It exhibits a higher energy (140 Kev) than the materials employed with the RIGS system, however, this is not a significant characteristic, lower energy radionuclides having been used successfully.

The RIGS system is one wherein a hand-held radiation detecting probe is provided which preferably supports a cadmium zinc telluride detector or crystal of sufficient surface area to detect the minute levels of radiation involved in that procedure. Such a detecting probe is described, for example, in U.S. Pat. No. 5,070,878 by Denen, issued Dec. 10, 1991, and assigned in common herewith. This probe currently utilizes a cadmium zinc telluride crystal of the noted adequate surface area which is mounted in a "forward-looking" manner within a tubular probe body which has a sidewardly-directed cant of about 30° to facilitate its maneuvering in and about organs within the peritoneal cavity. As the probe is held by the surgeon, the window component thereof at its tip is moved along tissue being evaluated. During this surveying maneuver, as radiation is encountered, it is first evaluated for appropriate energy levels, and then statistically evaluated in terms of count rates. Where a statistically significant count rate is encountered, the probe is operated in an aural or sound mode manifested as a siren sounding to alert the surgeon. The noted statistical analysis of count rate is generally based upon a number of standard deviations above a base count rate. That computed level is referred to as a squelch threshold count rate value. The base count rate is developed by holding the crystal face of the probe against, for example, a region of the heart for an interval of five seconds to then generate an average count rate for that interval. Then, the software algorithm of the associated control unit, depending upon its operational mode, will establish the presence of tumor, for example, at a level of three standard deviations (three sigma) above the base count rate. This algorithm is described, for example, in U.S. Pat. No. 4,889,991, issued Dec. 26, 1989 by Ramsey and Thurston, entitled "Gamma Radiation Detector with Enhanced Signal Treatment", and assigned in common herewith which is incorporated herein by reference.

In contrast with the RIGS procedure, an advantage of the present technique is that the radiopharmaceutical is injected locally near the main lesion rather than intravenously. The result is that there is little general background but there is a high concentration in the lymph duct or ducts and corresponding nodes. The relatively high activity results in high count rates and a smaller diameter detector is quite feasible.

FIG. 1 reveals the system 10 under which the node identification technique may be implemented. Configured for utilization in conjunction with the identification of sentinel lymph nodes, the system 10 includes a now somewhat conventional control apparatus or unit represented at 12. The apparatus 12 is described, for example, in U.S. Pat. No. 4,801,803, entitled "Detector and Localizer for Low Energy Radiation Emissions", by Denen, Thurston, and Ramsey, issued Jan. 31, 1989, assigned in common herewith and incorporated herein by reference. Extending from a coupling or connector 14 on the forward face 16 of apparatus 12 is a flexible connector or cable 18 which provides power supply, crystal detector bias signal, return line, and ground to a hand manipular probe 20 by virtue of its connection therewith at a coupling or connector 22. Such connectors may be provided as a D series Model EGG connector marketed by Lemo USA, Inc., of Santa Rosa, Calif. The probe 20 is configured for retaining a cadmium zinc telluride detector crystal in substantially the same manner as discussed above in connection with U.S. Pat. No. 5,070,878, but is of smaller diameter and has a lengthwise extent of about 6 in. (15.24 cm). Positioned on the housing 24 of probe 20 are two sealed piezoelectric switches 26 and 27 which are located preferably just rearwardly of the middle of the probe. These switches may be activated by the clinician or surgeon for the purpose of carrying out either of two functions associated with the control apparatus 12.

Control apparatus 12 also incorporates a serial port which is shown connected via serial communication cable 30 to an input/output card provided with a conventional personal computer (PC) represented generally at 32 and incorporating the conventional computer console 34, a keyboard 36 associated with console 34 by cable 38, and a monitor 40 having a display assembly 42. Display assembly 42 is shown displaying a dynamic graphics output represented generally at 44.

Also coupled to the control console 12 by a cable 46 is a manually controllable threshold (squelch background) adjusting device represented generally at 48 and shown including a housing 50 and two sealed piezoelectric button type switches 52 and 53. Indicia are positioned upon the housing 50 in the form of an up arrow in association with switch 52 and in the form of a down arrow in association with switch 53 as seen, respectively, at 54 and 55. Device 48 may be employed in a mode of operation of system 10 seeking the precise location of a sentinel lymph node within a drainage basin or a regional node locale.

Returning to the control assembly or control unit 12, the forward face 16 thereof is seen to carry a relatively large LCD readout or display 60, a dual colored LED readout 62, and a sequence of finger actuated switches represented generally at 64. This switch array 64 or keyboard permits the microprocessor driven control unit 12 to carry out an instructive or "user friendly" dialogue with the practitioner. In addition to conventional on and off switches shown, respectively, at 66 and 67, the switches provided at forward face 16 include such function selection switches as a count mode switch 68, a sound switch 69, a reset count switch 70, a statistical significance level selection or ranging switch referred to by the term "squelch" 71, a calibration switch 72, and up and down incrementing switches for adjustment within certain of the switch generated modes as shown, respectively, at 73 and 74. Of the switch array 64, reset count switch 70 and "squelch" switch 71 are, to an extent, replicated upon probe 20 as switches 26 and 27. In this regard, one of the switches as at 26, when actuated, carries out the function of reset count switch 70. That function is to derive a count value over a preset interval, for example, 5 seconds. The second of the switches on probe 20, as at 27, carries out an emulated switching sequence initially of squelch switch 71 followed by an actuation of reset count switch 70. This permits the system 10 to re-establish a base count rate and threshold above that rate with a singular switch actuation.

In similar manner, switches 52 and 53 of device 48 serve, inter alia, to replicate the respective up and down switches 73 and 74 upon the console unit 12. Piezoelectric switches which can be sealed are employed with the unit 48 such that it can be located during surgery in the surgical field. In this regard, the sealed switches 53 and 54 can be appropriately sterilized by autoclaving procedures or the like. In its normal operation, when the control unit 12 is in a squelch mode entered by actuating switch 71, the squelch count rate threshold level can be adjusted incrementally upward by actuating switch 73 and incrementally downwardly in value by incrementing switch 74. The upper end of this manual adjustment range is limited to reduce the chance of inadvertently setting the squelch background threshold excessively high to render the system essentially inoperable. The maximum manual adjustment range is approximately three times the square root of the two second equivalent of the last occurring five second standard squelching operation. Minimum value squelch background attainable using the down arrow switch 74 is equivalent to 25 counts in a 5 second interval.

Looking to FIG. 2, a more detailed representation of the probe device 20 is revealed. As noted above, probe 20 is more diminutive in size than the conventional RIGS probe and is not canted at its forward tip. This straight and thinner structuring facilitates its employment, inter alia, in detecting and locating or pinpointing sentinel nodes. The device 20 utilizes a cadmium zinc telluride crystal which, necessarily, is of lesser diameter, for example 7 mm. to provide a forward-looking surface area of about 38.48 $mm^2$. This lesser surface area remains practical in extent for the instant applications in view of the higher intensity level of the radionuclides employed with the system, for example, $^{99m}T_c$. The housing or gripping portion 80 of the probe is formed of stainless steel in the general configuration of a hollow right cylinder. A forward cap or cover 82 is mounted upon the body portion 80. Cap 82 is configured having a forward looking window 84 of lesser thickness. Positioned immediately adjacent the crystal retaining components of the probe 20 at its cap 82 is a small circuit board forming a detector assembly with the crystal and carrying a preamplification function as well as bias to the detector crystal. Cable 18, shown connected to the probe 20 at a Lemo connector 18, provides the noted detector bias, ground, preamplifier output signals, and preamplifier power, certain leads from the cable 18 being shown at 90. The power supply lead of this grouping 90 is tapped by switches 26 and 27. Switches 26 and 27 are of a piezoelectric variety, generating a voltage when actuated. To assure their integrity with respect to their operational environment (surgery and gas sterilization), the switches preferably are mounted within housing 80 to assure sealing them against fluid and gas leakage at the switch positions. Thin windows provided as diminished wall thicknesses may be located upon the housing 80 to permit a flexure over the piezoelectric switches to carry out their actuation. Flexible aluminum dome structures also are available for such switching. The same arrangement may be provided with respect to device 48 to protect the integrity of the circuitry in switches therein, for example, during sterilization procedures as well as in the course of use of the device within the surgical field. Such switch components are available, for example, from Wilson-Hurd Company of Wansan, Wis.

Referring to FIG. 3, a sectional view of the forward portion of probe 20 is revealed. The figure shows that the components of the probe are arranged symmetrically about a longitudinally disposed orientation or probe axis 92. While the "straight" or non-canted version of the probe device 20 represents the preferred embodiment thereof for the instant purpose, the axis may be canted to remain perpendicular to window 84 and the detector surface just below it. The forward potion of housing 80 is shown necked down at 94 to provide a cylindrical receiving surface for the cap 82. Additionally, the annular end surface 96 of the housing 80 serves to provide an aligning and abutting support for a generally cylindrically shaped slug or crystal mount 98. Formed of lead, the mount 98 includes a cylindrical rearward portion 100 which is slideably received within the inner surface of housing 80. This cylindrical support portion 100 terminates at an annular shoulder 102 which abuts against end surface 96 of housing 80. Thus mounted, the crystal mount 98 may be retained in position, for example, with an electrically conductive epoxy cement. A passageway or bore 104 is formed through the mount 98 such that it extends into a cavity 106 formed therein. A cross bore 108 also is formed within the retainer 98 to equalize gas pressure within probe 20, and an annular groove 110 is formed forwardly of the bore 108. Positioned centrally within the cavity 106 is a cadmium telluride crystal detector 112 which is of generally cylindrical form, the forward surface 107 of which is in a plane perpendicular to axis 92, is mounted in a cushion-like arrangement to avoid motion generated noise. With the arrangement shown, probe axis 92 also becomes a detector axis, inasmuch as it is perpendicular to the plane of the crystal's forward surface 107. A cushion mount is provided because, in general, cadmium telluride crystals may exhibit microphonic (piezoelectric) effects and are very fragile. CdTe crystals may be alloyed and still are referred to as "cadmium telluride" or "CdTe" crystals for present purposes. A preferred cadmium telluride crystal is formed as a CdTe material alloyed with zinc and generally represented by the expression: $Cd_{1-x}Zn_xTe$. Proportioning of the Cd component and Zn component of the crystals may vary to provide an effective ratio selected to suit the particular requirements of the user. However, a lower limit or boundary for the proportion of zinc where x equals about 0.2 has been determined, while a correspondingly high boundary or limit wherein x equals 0.8 has been determined. The alloyed crystals are marketed, for example, by Digirad, Inc., San Diego, Calif. 92067, and eV Products, Saxonburg, Pa. 16056.

Returning to FIG. 3, passageway 104 is seen to receive a Teflon insulated multi-strand lead 114 which serves to carry the noted bias signal as well as those charge signals generated from the crystal assembly. For providing a cushioning of the crystal 112, a mounting approach is employed which includes an in situ formed electrically insulative layer of generally cup-shaped configuration shown at 116. Cup-shaped layer 116 may be formed of silicone, generally referred to as silicone rubber which is an elastomer in which the C linkages of a polymerized hydrocarbon are replaced by Si—O linkages. It is sold, for example, under the trademark "Silastic". The forward facing surface 118 of layer 116 is coated with additional mounts of the silicone material as at layer 120, and the pattern of multiple strands 122 of lead 114 are spread out in a disk-shaped array over this layer 120. Additionally positioned over the forward surface 118 at the bottom of cavity 106 is an electrically conductive cushion layer 124, the lower disposed surface of which is positioned over the strands at 122. Preferably, cushion layer 124 is provided as a non-woven Teflon cloth which is carbon filled to the extent rendering it an effective conductor of electricity. In general, the material is a carbon containing stretched, highly crystalline, unsintered polytetrafluoroethylene marketed under the trademark "Gore-Tex". With this arrangement, bias can be asserted at the rearward face of crystal 112 without generation of metal-to-crystal induced noise. Crystal 112, as noted above, has a surface area smaller than that mounted with the standard RIGS device but selected in correspondence with the size, i.e. general diameter or principal dimension of a typically encountered lymph node. Further, to accommodate the radionuclides of higher energy encountered with sentinel node tracking and differentiation procedures, the crystal 112 is made thicker, for example being 2.0 mm in thickness as opposed to the 1.5 mm thickness of the detector within the RIGS probe. As in the RIGS probe mounting, the sides of crystal 112 are slightly spaced from the corresponding sides of the cup-shaped layer 116. This presents a form of gap as represented at 126. The gap 126 serves to aid in the avoidance of noise induced by rubbing. A small mount of the silicone comprising layer 120 may invade the gap 126 with beneficial effect.

Ground is applied to the forward face 107 of crystal 112 in conjunction with a compressive retention arrangement. In this regard, two, somewhat hoop-shaped fine silver-plated copper wires, one of which is represented at 128, are conformed in non-crossing fashion over the surface of the crystal 112 and mount 98. These fine wires are retained in position at the annular groove 110 by an O-ring 130. Inasmuch as the wires as at 128 are coupled with the mount 98, they are held at ground potential. This grounding potential is asserted to the forward surface of crystal 112 through two conductive and compliant members 132 and 134 which are disk-shaped, member 132 having the same configuration as the forward surface 107 of crystal 112, and member 134 being of lesser diameter. This provides for a more even application of compressive force into the forward surface of crystal 112. Members 132 and 134 may be formed of the earlier-described material provided at compliant member 124. The entire arrangement of crystal 112 and component 124, 132, 134, and wires as at 128 are retained in appropriate position in an overall compressive fashion by a resilient retainer 136 which is positioned in tension over the entire assembly and retained in such tension and position by the noted O-ring 130. Resilient retainer 136 may be provided as a web of nylon or the like. This web is positioned over the assemblage components and drawn downwardly over them as well as over the outer surface of crystal mount 98 in the course of fabrication of the probe device.

Forward cover 82 is positioned over the above-described assembly. This cover is formed of a convenient radiation transmissive material such as aluminum. Utilization of such transmissive material for the entire cover is permissible inasmuch as the sides of the crystal retaining cavity of crystal mount 98 block radiation from all directions except the forward face 107 of crystal 112. Because the cover 82 functions as an electrical shield, the interior side surfaces thereof may be made electrically conductive by the deposition thereon of a thin layer of gold. It may be observed in the figure that upon final assembly of the probe, a gap as at 138 is located between the window component 84 and the retainer 136 which serves as a dead air space. This dead air space provides an enhancement of acoustic isolation of the detector 112.

While the "straight" or unbent embodiment for the probe 20 as shown in the drawings represents the preferred device for use with the instant method, the method can be performed in conjunction with probes wherein the forward surface of crystals as at 112 are canted with respect to the graspable or handle portion of the probe. For example, as used in the conventional RIGS instrumentation discussed above. Where such use is made of that earlier-developed instrumentation, then the detector axis would be considered to remain in an orientation perpendicular to the forward surface of the crystal detector. This is because the orientation of the crystal as at 112 functions to point to the sentinel node.

In view of the possible adjacency of radiation emitting regions which may occur with the present system, some practitioners may find it valuable to utilize a collimator in conjunction with probe 20. Looking to FIG. 4, such a collimator is represented generally at 140. Formed of a radiation attenuating material such as tungsten, the collimator 140 is configured having a relatively thicker cylindrical rearward portion 142 which is tapered at region 144 toward a circular opening aperture 146 having a diameter corresponding with the diameter of crystal 112 and extending as a bore 148 to window 84. An annulus-shaped shoulder 150 is seen to abut against the outer periphery of window 84. Generally, the collimator 140 is employed where the probe 20 is being utilized in somewhat close adjacency with a source of radiation other than that being investigated.

Figure 5A:
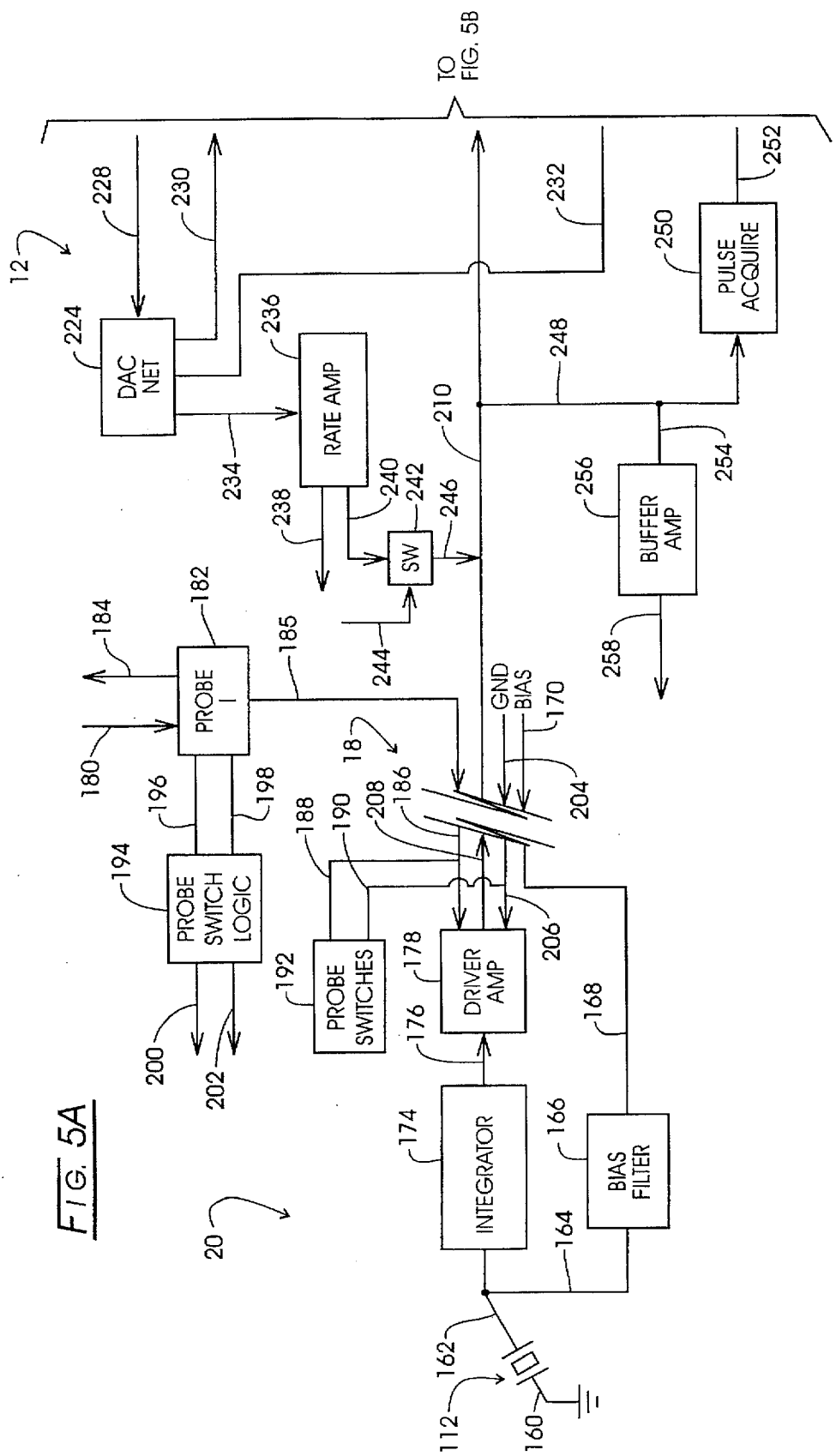
FIGS. 5A and 5B combine as labeled to provide a block diagrammatic representation of the circuits employed with the control assembly and probe shown in FIG. 1.
Figure 5B:
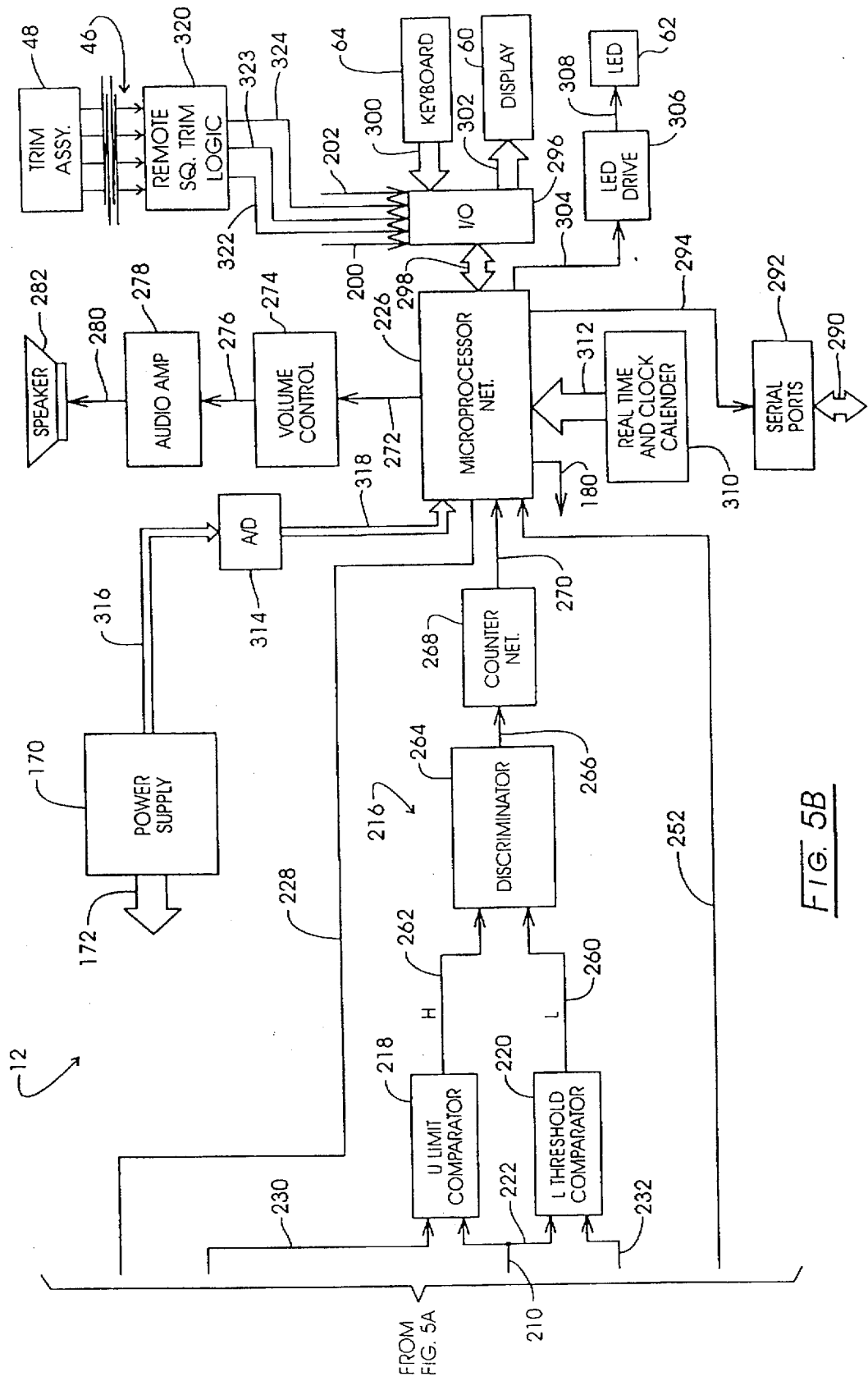

Referring to FIGS. 5A and 5B, a block diagrammatic representation of the circuitry employed with system 10 is portrayed. These figures should be considered in mutual adjacency in the manner labeled thereon. In FIG. 5A, the cadmium telluride crystal 112 is shown having one face coupled to ground through line 160, while the opposite, biased face thereof is coupled via lines 162 and 164 to a bias filter represented at block 166. The input to filter 166 is represented at line 168 as being applied through the cable as described earlier at 18, which numeral reappears in the instant figure. The bias input is seen, as represented at line 170, to emanate from a multi-output power supply shown in FIG. 5B at block 170. These various outputs are represented in general by an arrow 172 as seen in the latter figure. Returning to FIG. 5A, line 162 from the crystal 112, carrying detector outputs corresponding with radiation emissions impinging upon the detector 112 is seen to extend to an integrator stage 174. This integrator stage 174 forms part of the preamplification function mounted at circuit board 86. The integrated valuation of detected radiation emissions then is shown directed as represented by line 176 to a driver amplification network shown at block 178. A preferred preamplification circuit comprised of blocks 174 and 178 is described in U.S. Pat. No. 5,441,050, by Thurston, et al., issued Aug. 15, 1995, entitled "Radiation Responsive Surgical Instrument", which is assigned in common herewith. A d.c. power supply is provided from the power supply represented at block 170 (FIG. 5B) and arrow 172 for the preamplification function. This power supply is directed, as represented at line 180 to a probe current network represented at block 182. Under microcomputer control as represented at line 184, the network 182 develops signals, for example, determining whether the probe instrument 20 has been properly connected to the console or control unit 12. Delivery of the d.c. power supply for the preamplification function is represented at lines 185 and 186. Line 186 forms a component of flexible cable 18. Connected with line 186 is one line of the outputs of probe switches 26 and 27 as represented at line 188 shown directed to the probe switches and associated networks represented at block 192 the second line from block 192 is shown at 190 which is connected to instrument ground at line 206. In general, when a piezoelectric switch 26 or 27 is actuated, a switch voltage signal is generated which is directed to a current deriving voltage comparator circuit having an output coupled, as represented at lines 188 and 190 with the power supply input line 186. The switch voltage signal generated by the piezoelectric switches, performing with the comparator circuit, functions to impose a current signal of predetermined amplitude at line 186 which is detected by probe switch logic circuitry represented at block 194. Network 194 monitors the current excursions present at line 185 as represented by monitoring lines 196 and 198. The logic represented at block 194 includes a monitoring amplifier stage and a level comparator circuit which function to provide function input signals corresponding with the actuation of either switch 26 or switch 27 at respective output lines 200 and 202. For the present embodiment, the output at line 200 represents an actuation of the reset count switch and an output at line 202 represents an actuation of the squelch switch. When the squelch switch 27 is actuated on probe 20, the logic in block 194 produces a sequence consisting of the assertion of a signal on line 202 followed, after a short delay, by an assertion of a signal on line 200. With the implementation of the probe switches as represented at block 192 as well as the probe switch logic represented at block 194, the pre-existing power supply line of flexible cable 18 is utilized and no additional wiring is required for that component of system 10. This is advantageous inasmuch as it is important that this cable 18 remain as diametrically small and flexible as possible. Ground to the probe 20 is developed from the power supply as represented at respective block 170 and arrow 172, and is shown in FIG. 5A as being provided along lines 204 and via cable 18 along line 206. The preamplification stage derives count outputs which are presented along line 208 and cable 18 for introduction to the control unit 12 as represented at line 210. Line 210 extends to the input of an energy window network represented in FIG. 5B in general at 216. Looking additionally to FIG. 5B, it may be observed that energy window network 216 includes an upper limit comparator represented at block 218 as well as a lower threshold comparator represented at block 220. The count output or photon event signals at line 210 are submitted simultaneously to each of these comparator functions 218 and 220 as represented at line 222. Correspondingly, the comparison values or limits associated with the upper limit comparator 218 are applied from a digital-to-analog converter (DAC) seen in FIG. 5A at block 224. Converter 224 is under the control of a microprocessor network represented at block 226, such digital control to device 224 being asserted as represented at line 228. Thus, the upper limit value asserted at comparator 218 is provided as represented at line 230, from DAC 224. Correspondingly, the lower threshold value for comparator function 220 is asserted from DAC 224 via line 232.

The microprocessor network 226, also as represented by line 228, also develops an analog signal at DAC 224, as represented at line 234 which corresponds with instantaneous pulse rate. This information is conveyed to a pulse rate amplifier network represented at block 236. The output of rate amplifier function 236, as represented at line 238 may be provided at the rear of control unit 12. The circuit represented at block 236 also may be employed to generate a calibrating pulse for testing the downstream components of the system. Thus, the microprocessor network 226 may apply a predetermined pulse level through the digital-to-analog conversion network 224 for presentation to the amplifier network at block 236. The resultant output at line 240 is selectively switched as represented at block 242 to provide a pulse width definition. In this regard, the switching function represented at block 242 is regulated as represented at line 244 from microprocessor network 226 and the pulse categorized signal from switch function 242 is introduced to line 210 as represented at line 246.

The signals at line 210 also are directed, as represented at line 248, to a pulse acquire function represented at block 250. Network 250 functions, when activated by the microprocessor function 226, to acquire the value of the highest pulse amplitude witnessed at line 210. Periodically, this information then is transmitted to the microprocessor function 226 as represented by line 252. Representing a form of peak detector, the network 250 sometimes is referred to as a "snapshot circuit". Also produced from line 248 as represented at line 254 and block 256 is a buffer amplifier which will provide at line 258 an output representing received pulses which may be made available at the rearward portion of console or control unit 12 for conventional radiation evaluation purposes.

With the arrangement shown, the probe 20 assemblage derives count outputs in response to photon emissions which are confronted at crystal 112. Those count output signals will have an amplitude corresponding to the energy of interest of the photon emissions. Additionally, the signals may represent spurious phenomena such as cosmic rays and the like. Accordingly, the energies of the count outputs or amplitudes thereof are evaluated at the energy window network 216 seen in FIG. 5B. The lower threshold comparator function 220 will promulgate a pulse of fixed and consistent duration identified as "L" at line 260 when the signal asserted thereat exhibits an amplitude of value equal to or above a threshold value. That threshold value is established, as noted above, from line 232. Correspondingly, the count output signals from line 222 will be evaluated by the upper limit comparator function 218 such that when the count output signal exhibits an amplitude of value above the upper limit value established from line 230, a pulse of consistent and fixed duration identified as "H" will be promulgated at line 262. These outputs from lines 260 and 262 then are directed to the input of an asynchronous, sequential, fundamental mode discriminator circuit represented at block 264. Circuits as at 264, while being sequential in nature, are not synchronized in any way with a clock signal. Such circuits as at 264 are described, for example, in U.S. Pat. No. 5,475,219 by Olson, entitled "Validation of Photon Emission Based Signals Using an Energy Window Network in Conjunction with a Fundamental Mode Discriminator Circuit", issued Dec. 12, 1995, and assigned in common herewith. The discriminator function 264 serves to generate photon event outputs or count associated signals in the form of finite pulses at line 266 upon the occurrence of a count output signal at line 210, which represents a photon emission which is valid from the standpoint of the energy range of interest associated with it. These pulses at line 266 then are counted by a counter function represented at block 268, whereupon, as represented at line 270, the count data as evaluated by the input network heretofore described is submitted to the microprocessor network 226 for statistical analysis. The function of counter network 226 may be implemented in software as described in the above-referenced U.S. Pat. No. 4,889,991. Microprocessor network 226 performs under a variety of operational modes depending upon the user inputs to the function switches 64 on the control unit 12. In general, it functions to provide outputs to two output components, one aural type generated from a speaker, and the other a visual output at display 60. Generally, a "siren" type signal manifested with a predetermined frequency variation is asserted first to a volume control function represented at block 274 whereupon the volume adjusted signal is directed as represented at line 276 to an audio amplification circuit represented at block 278. Circuit 278, in turn, as represented at line 280, drives a speaker 282. With the noted siren arrangement, the frequency output from speaker 282 increases with an exponential change from 20 Hz to 1200 Hz when the average count rate determined by system 10 exceeds a preset threshold level which is statistically significant over background count rates. The siren mode is accessed by the user either from control unit 12 by sequentially actuating squelch switch 71 and then reset count switch 70, or by actuating switch 27 on probe 20. For sentinel node identification, this siren mode feature is utilized for directing the surgeon to move the probe 20 and then carry out a squelching process by actuating switch 27 and reiterating that procedure until the range of movement becomes quite small. At that position the resultant "circle of sound" will be effective to the extent that the axis 92 of probe 20 will be pointing directly at the sentinel node and will be responding to a peak count rate. The siren mode of performance is described in detail in the above-referenced U.S. Pat. No. 4,889,991, by Ramsey and Thurston. In the RIGS general procedure, following the sequential actuation of switches 71 and 70, the count output of probe 20 is evaluated for an interval of 5 seconds to establish a base count rate. Then the program of the microprocessor network 226 establishes a predetermined statistical threshold count rate above that base count rate such that the aural output from speaker 282 will not be effected until that predetermined statistically significant count rate level is reached. Thus, by carrying out this procedure, for example at the periphery of the location of the sentinel node and then by continuing movement until the output extends from silence at the squelch location, then to sound, then to silence or a low frequency output, the sentinel node can be located both in a transverse directional sense and in the sense of depth as the probe 20 is moved into the mass of tissue in which the sentinel node is located. In the latter regard, from the generalized node carrying source of radiation, the emission rate available for counting will increase in accordance with the inverse square law of radiation propagation as the detector 112 of probe 20 approaches the sentinel node. The same result can be obtained in an alternate mode of operation wherein the operator trims the threshold incrementally to a higher threshold rate value from the manually actuated device 48 by pressing switch button 52. This avoids a need for the five second base rate count provided with the siren mode of operation.

Figure 6:
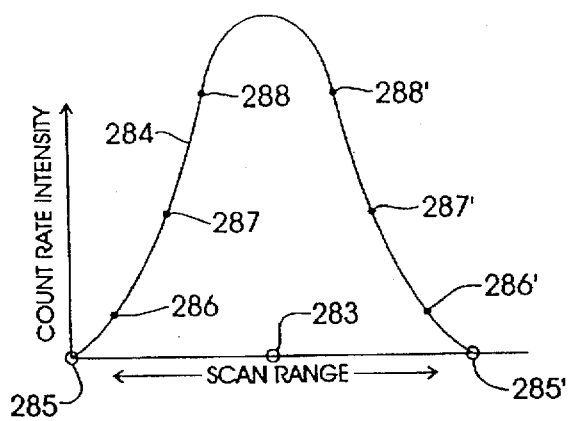
FIG. 6 is a scan range versus count rate intensity curve demonstrating the guidance technique employed with the method of the invention.

This technique for locating the sentinel node by developing an ever decreasing squelch defined range of scan may be portrayed graphically. Looking to FIG. 6, count rate intensities during a scan over, for example, the regional node basin containing a sentinel node is plotted against the distance the probe is used in scanning over that region. The sentinel node, now carrying a concentration of radiopharmaceutical, will be located somewhere within the tissue but at the highest point of count rate intensity encountered in a scan. This midpoint is located at 283 in the drawing and the count rate intensity may be portrayed by the curve 284. With the procedure, a conventional squelching action, i.e. pressing or actuating switch 27, is carried out at a periphery of this region, for example at point 285 or 285' depending upon the direction of movement of probe 20. The probe then is scanned from one edge to the other of curve 284, essentially a procedure where the probe is initially silenced then aural sound is heard, then silence again or a very low frequency is encountered in a scan from point 285 to 285'. The probe will be over the sentinal node midway between points 285 and 285'. Accordingly, the probe is moved inwardly from either of these positions as at 286 and 286' and the squelch switch 27 is actuated to remove the sound output by elevating the squelch threshold. Note that the range now has narrowed and the probe still will be over and pointing down toward the sentinel node when it is over the midpoint 283. The surgeon again may move the probe inwardly, for example, to location 287 or 287' and again carry out a squelching procedure. A subsequent scan between those points again is one of narrowed range to bracket the location of the midpoint 283 over the sentinel node. A squelching procedure again may be carried out by moving the probe inwardly from the last point of squelching, for example to scan between points 288 and 288'. Such a scan will show a very narrow circle of sound. At this juncture, only slight movement of the probe is required to complete a traverse and the location of the sentinel node is readily determined. This same procedure then is carried out in terms of three-dimensional movement through an incision toward the sentinel node.

The control system embodied within the console 12 as utilized with the RIGS surgical system includes a feature not used with that surgical system wherein the previously existing squelch threshold value can be trimmed upwardly or downwardly in count rate value. While not employed with a conventional RIGS surgical procedure, the feature may be used for the purpose of swiftly elevating the squelch threshold count rate by increments. This squelch trim mode may be utilized manually with respect to console 12 by first actuating the squelch switch 71 shown in FIG. 1 and within an ensuing 7 second interval actuating one or the other of the up or down incrementing switches 73 and 71. The amount of incrementation varies with the maximum count rate found in conjunction with an initial 5 second conventional squelching procedure. In general, the incrementation is a value corresponding with the interval of the base squelch count rate. By holding one of the switches 71 or 73 down for an extended period of time, the increment will be added or subtracted depending upon the switch employed in a succession occurring at a rate slightly less than one increment per second. Count rate limitations are imposed with the feature such that the upper squelch limit cannot exceed a practical value. Thus, the conventional 5 second squelch procedure may be carried out to re-establish the range for incrementally elevating the threshold value. Similarly, incrementation to lower threshold values is limited, for example, to about 25 counts per second. Device 48, while being sterilizable and thus usable within the sterile field emulates this procedure by, in effect, in succession, carrying out the actuation of squelch switch 71, followed by an actuation of the selected up or down switch 73 or 71, now as represented by singular switches 52 and 53. The procedure advantageously lessens the amount of time the surgeon is required to utilize in the overall scanning approach, time representing a highly important aspect of any surgical procedure.

Count rate values developed from the microprocessor network 226 also are directed from serial ports 292 and cable 30 as represented by dual arrow 290 to the general purpose computer 32 for purposes of mapping that lymph carrying duct which is carrying radiation emitting fluid toward the sentinel node. For such purposes, an incision need not be made to locate the duct and peak count rates may be visually ascertained at the display 42 of monitor 40 as probe 20 is moved about the epidermis. As this movement of the probe for the purpose of lymph duct mapping is carried out, the count rate display graphics as at 44 scroll, for example, from right to left, as the probe is moved along the epidermis of the patient, a peak being displayed in the graphics 44 in general as the probe passes over a lymph duct within which radionuclide containing fluid has migrated.

Microprocessor network 226 performs in conventional fashion with an input/output network as represented at block 296 and dual directional arrow 298. This input/output port function provides appropriate scanning of keyboard or switches 64 at represented at arrow 300. These switch inputs or function inputs are emulated by probe carried switches 26 and 27 as represented by the reoccurrence of probe switch logic output lines 200 and 202 being directed to block 296. The output port also drives the display 60 at represented by arrow 302. During a counting operation, the microprocessor network 226 functions to control a light emitting diode drive network as represented by line 304 extending to LED drive at block 306. The drive network represented at block 306 is shown providing an output, as represented by line 308, to the dual LED display as described at 62 in FIG. 1 and represented in block form with the same numeration. The readout provides a red light when a gamma ray is detected, and a green light during counting procedures. A real time clock-calendar having a non-volatile memory also may be provided in conjunction with the function of the microprocessor network 226 as represented by block 310 and arrow 312. Further, the microprocessor network 226 may be employed to monitor the performance of the power supply represented at block 170. This is shown being carried out by the interaction of the microprocessor network 226 with an analog-to-digital converter represented at block 314 and having an association represented by arrows 316 and 318. As is apparent, the converter 314 functions to digitize analog values at the power supply 170 for submittal to network 226.

Trim assembly 48 is shown at FIG. 5B in block form with the same identifying numeration. Additionally, cable 46 which is coupled into console 12 is represented as a four line array. These input lines will include +12v, ground, an up trim switch actuation signal from switch 52, and a down trim switch actuation signal from switch 53. Cable 46 is coupled to a remote squelch trim logic circuit represented at block 320. Circuit 320 provides three outputs at lines 322–324 which are seen directed to block 296. The logic of circuit 320 will be seen to function to cause the equivalent of a switching action of squelch switch 71 through the expedient of coupling an open collector configured transistor across the switch contacts. Following actuation of that switch for a predetermined interval, a delay interval ensues whereupon a similar action occurs with respect to either up arrow switch 73 or down arrow switch 74. The logic circuit 320 also functions to emulate a continuous closure of either of the up or down switches to permit the successive incrementation feature of control unit 12 to be carried out.

The piezoelectric switches 26 and 27 on the probe device 20 generate voltage outputs which, in turn, are associated with circuits which develop predetermined current levels which are imposed upon the power supply lead of the cable 18 and are monitored for their amplitudes by supplementary circuitry within the control assembly or control unit 12. In general, switch 26 may be arranged to produce about 1.5 milliamperes to represent a reset count actuating signal while switch 27 will generate a pulse of current three or four times greater than that. These pulses or abrupt increases in the current flowing within the 12v power supply line then are detected in a circuit represented in FIG. 8

Figure 7:
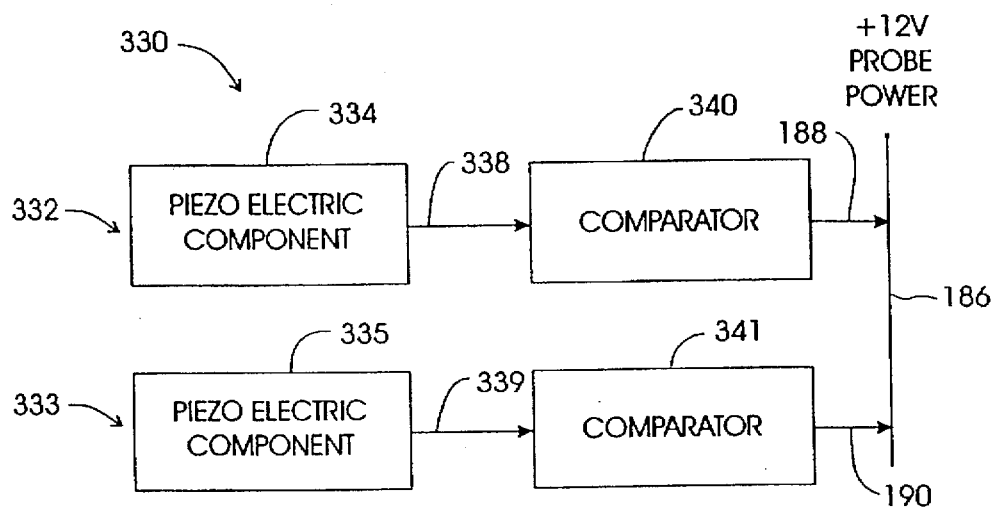
FIG. 7 is a block diagrammatic depiction of switch circuits employed with the probe shown in FIG. 1.

Turning to FIG. 7, a block diagrammatic representation of the two somewhat identical circuits which are utilized to produce the above-noted current pulses with respect to switches 26 and 27 is revealed in general at 330. The two circuits again are represented in general at 332 and 333 corresponding, respectively, with reset count switch 70 and squelch switch 71. The piezoelectric components of switches 70 and 71 as well as associated protective circuitry are represented at respective blocks 334 and 335. In addition to incorporating a piezoelectric switching device, each of the components 334 and 335 include series coupled resistors for protection against relatively larger voltages which may be encountered should the probe 20 be dropped or otherwise physically shocked. Additionally, such devices as a Zener diode are additionally incorporated to provide surge protection. The output of piezoelectric components 334 and 335 are presented as represented at respective arrows 338 and 339 to a comparator represented at respective blocks 340 and 341. When the piezoelectric device contained within components 334 and 335 is pressed, a voltage will be generated, for example, as high as about 6 volts. In response to this input, and depending upon their particular configuration, comparators 340 or 341 will respond to produce a negative going signal, for example dropping from +12v to about 0 volts to produce a pulse of current on the power supply line above the approximately 16 milliamps normally required by the preamplification function within probe 20.

The outputs of comparator stages 340 and 341 are presented, as described in connection with FIG. 5A at lines 188 and 190 to the power supply input line 186, those three lines being identified with the same numeration in FIG. 7. A more detailed description of the circuit shown at 330 is provided in a copending application for United States patent entitled "Remotely Controlled Apparatus and System for Tracking and Locating A Source of Photo Emissions" by Thurston, et al., assigned in common herewith and filed of even date herewith, Ser. No. 08/543,032.

Figure 8:
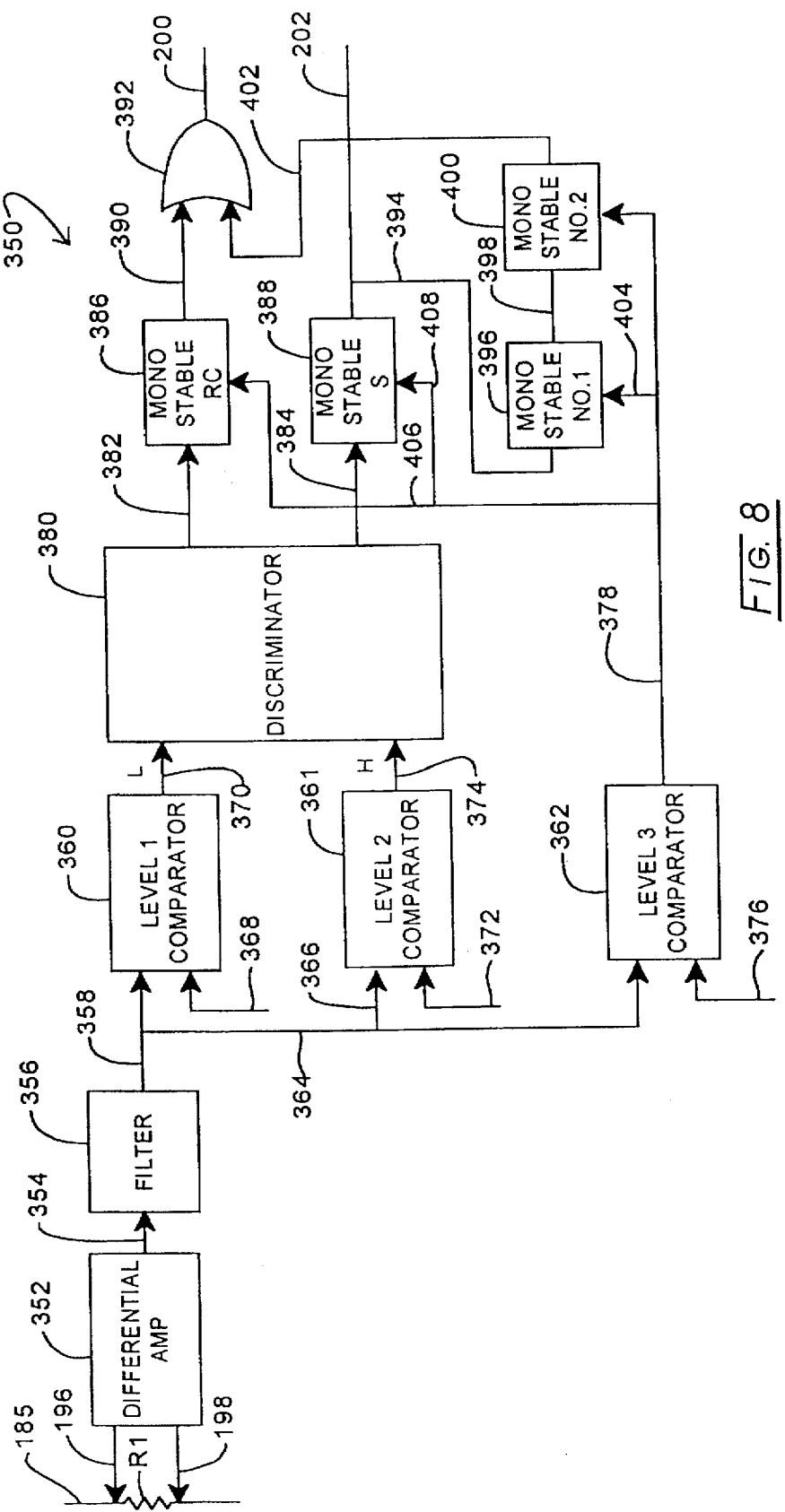
FIG. 8 is a block diagrammatic representation of a circuit functioning to develop signals emulating a reset count and squelch switch function of the control assembly shown in FIG. 1.

Referring to FIG. 8, a block diagrammatic representation of circuitry 350 which develops the signals emulating the noted reset count and squelch switch functions is portrayed. Circuit 350 monitors current flow within the probe current function 182 of control unit 12. In this regard, earlier described lines 196 and 198 are reproduced as monitoring the voltage induced in a resistor R1 within power supply line 185–186. Lines 196 and 198 extend to a differential amplification function represented at block 352. The amplified output thereof as represented at line 354 is presented to a filtering form of network represented at block 356. Within this function represented at block 356, an RC circuit exhibiting a relatively lengthy time constant is employed to remove the d.c. term which generally represents current flow to the preamplification function, as opposed to the pulse categorized signals representing switching inputs. Also within the function at block 356 is an RC structured filter for blocking noise generated by bumping a piezoelectric crystal within probe 20. Without such blocking, the level comparing function of circuit 350 would be defeated. From the filter function at block 356, as represented at line 358, the voltage based pulses are submitted simultaneously to three comparator stages identified as levels 1–3, and represented at respective blocks 360–362. In this regard, line 358 addresses the level 1 comparator at block 360, while the level 2 comparator at block 361 is simultaneously addressed from lines 358, 364, and 366. The level 3 comparator at block 362 is addressed from lines 358 and 364. A threshold input to comparator function 360 is represented at line 368. This threshold is set as the lowest level and a pulse of amplitude sufficient to represent an output of switch 26, representing a reset counter input, will cause its triggering to provide an output of at line 370, which is identified as "L". In similar fashion, a threshold input to the level 2 comparator at block 361 is represented at line 372. This upper limit as established from line 372 is selected as of higher level than that provided at line 368, such that comparator 361 will respond to generate a pulse in the presence of an actuation of squelch switch 27 but not upon the actuation of switch 26. In the presence of a voltage pulse of at least such upper limit amplitude, then an output will be present at line 374 which is labeled "H". It may be observed that the level 1 comparator will provide the noted "L" output at line 370 in the presence of an actuation of switch 26 as well as in the presence of an actuation of switch 27. The level 3 comparator at block 362 receives an upper limit input as represented at line 376 which is much higher than that represented at line 372. The function of comparator 362 is to accommodate for a rapid current in-rush to the probe 20 when it is first attached to control unit 12 under the condition wherein the control unit is in an on state. The output of this comparator stage 362 is represented at line 378 and will be seen to carry out an inhibit function. The level 1 and level 2 comparator outputs, at respective lines 370 and 374 are directed to the input of a discriminator circuit represented at block 380. Discriminator 380 will respond to the "L" signals at line 370 as they occur with each actuation of either switch 26 or 27 as well as to the signal received at line 374 in response to the actuation of switch 27. The circuit then determines which switch 26 or 27 has been actuated and provides an output at line 382 in the event switch 26 has been actuated and an output at line 384 in the event switch 27 has been actuated. Preferably, the discriminator 380 is implemented as an asynchronous, sequential, fundamental mode discriminator circuit. Such circuits, while being sequential in nature, are not synchronized in any way with a clock signal. Of this circuit family, the fundamental mode form of circuits are defined as circuits with level inputs and unclocked memory elements. They are referred to, for example, as type 4 circuits as discussed, for example, in the publication: "An Introduction to Computer Logic" by Nagle, Jr., et al., Prentiss-Hall, Inc., Englewood Cliffs, N.J., 1975. The circuit at block 380 is in the preferred embodiment based upon a Mealy model wherein outputs are defined on the transitions between states as are discussed in conjunction with FIG. 10 herein. Because of this transitional-based model, the outputs at lines 382 and 384 are of short duration. Accordingly, the outputs at line 382 and 384 are subjected to a pulse stretching function as represented at respective blocks 386 and 388. The thus stretched pulse as developed at MONOSTABLE R.C. block 386 is directed as represented at line 390 to a logical ORing function as represented at symbol 392. This provides an output at earlier-described line 200 which emulates the actuation of reset count switch 70. The output of pulse stretching MONOSTABLE S block 388 is presented at earlier-described line 202 which is reproduced in the instant figure. This will provide an initial emulation of an actuation of squelch switch 71 at line 202. The output at line 202 also is directed via line 394 to the input of a monostable multivibrator identified as "MONOSTABLE NO. 1" and represented at block 396. Device 396 functions to interpose a delay, following which, an output is presented at line 398 which is directed to a monostable multivibrator identified as "MONOSTABLE NO. 2" and represented at block 400. The device represented at block 400 creates a pulse of equivalent width with that generated at line 390 and presents it via line 402 to the ORing function 392. With this arrangement, the control unit 12 will respond to an emulated actuation of switch 71 and then switch 70 to cause the system to enter a siren mode and carry out a base count over an interval, for example, of five seconds whereupon a count rate threshold of statistical significance is established above the rate represented by that base count.

Returning to the level 3 comparator function at block 362, where a noted very high amplitude pulse is received which is well above the limit established with the level two comparator function at block 361, then an inhibit signal is presented at line 378 for a preset duration selected to occur throughout such a high amplitude pulse. This signal functions to inhibit the operation of the monostable multivibrator functions represented at blocks 396 and 400 as represented by lines 378 and 404. Additionally, the pulse stretching functions represented at monostable blocks 386 and 388 are inhibited as represented by lines 378, 406, and 408.

Figure 9:
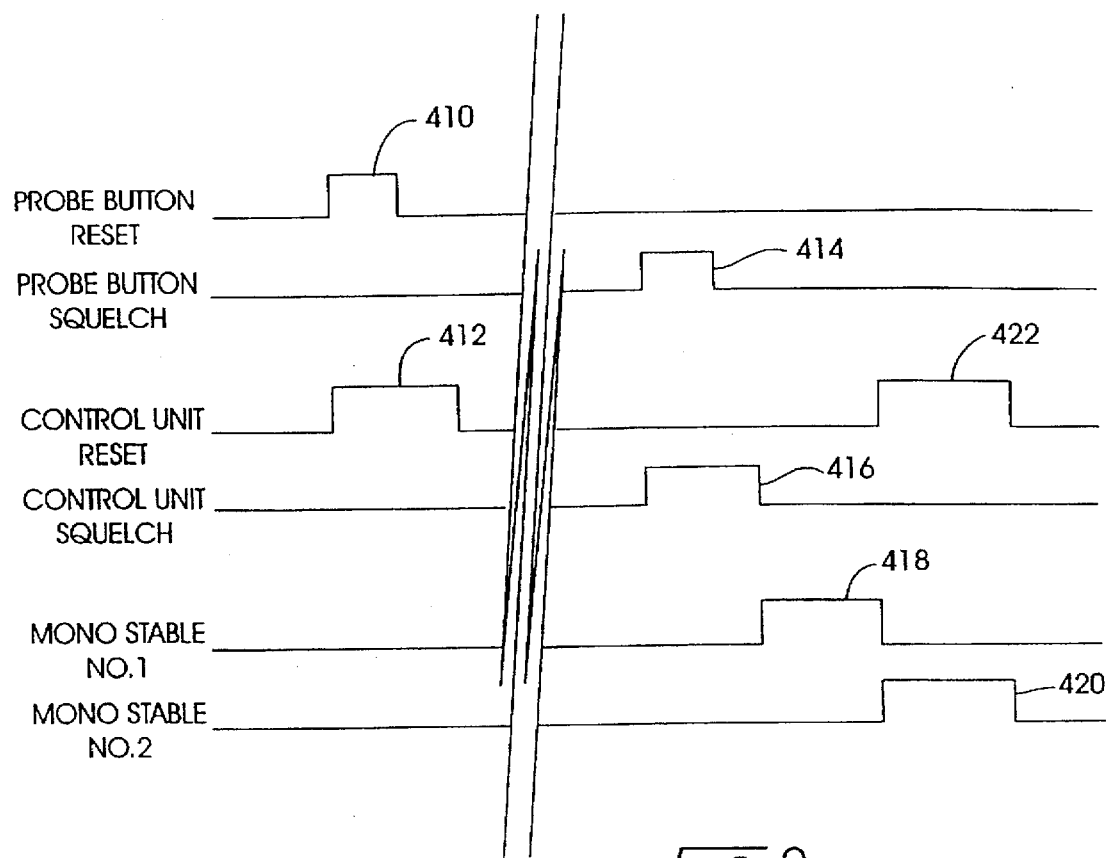
FIG. 9 is a pulse output diagram illustrating the performance of the circuit of FIG. 8.

Looking to FIG. 9, a signal or pulse output diagram showing the performance of circuit 350 is set forth. In the figure, the pulse output at line 382 corresponding with the actuation of reset counter switch 26 is represented at 410. The corresponding pulse directed from line 200 within the control unit 12 is shown as pulse 412 which has been subjected to the pulse stretching function 386. The actuation of the squelch switch 27 will create a pulse at line 384 which is represented at 414. This will create a corresponding pulse at line 202 emulating the actuation of squelch switch 71 and shown as a pulse 416. The falling edge of pulse 416 will trigger monostable multivibrator number 1 represented at block 396 to provide a delay interval represented as a pulse 418. The falling edge of pulse 418, in turn, riggers monostable multivibrator number 2 represented at block 400 which derives a pulse of fixed and known duration represented at 420 which is directed to the OR function 392 to provide that same pulse as a reset counter switch emulation shown as pulse 422, thus causing control unit 12 to enter a base count and count rate threshold setting mode of operation.

As noted above, a considerable advantage of the present arrangement is the utilization of a switching function with probe 20 but without the addition of additional wire strands within the probe cable 18. This permits a retention of the maximum amount of flexibility in that lengthy component.

Figure 10:
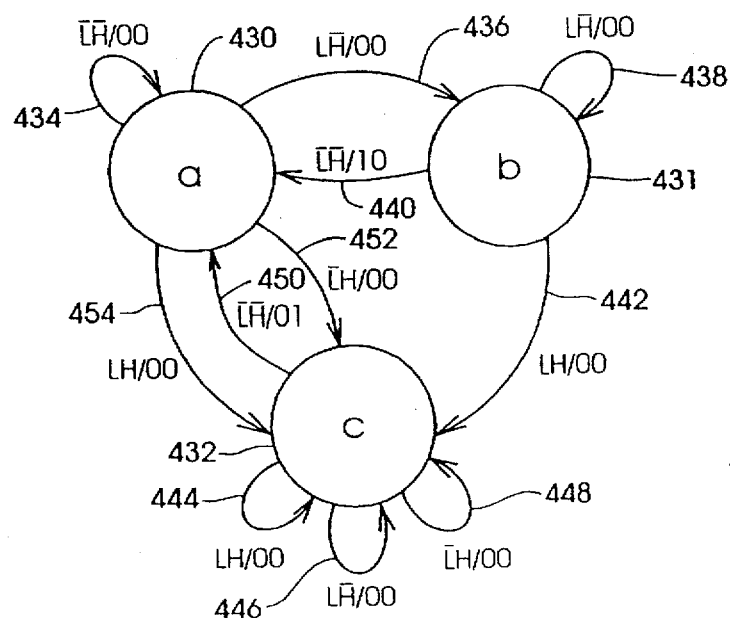
FIG. 10 is state diagram illustrating the performance of a discriminator circuit shown in block form in FIG. 8.

The asynchronous, sequential, fundamental mode discriminator circuit described in conjunction with block 380 in FIG. 8 may be described in conjunction with a state diagram. For this specific application, this circuit was designed with four states, a–d, however, one such state for the present circuit will never be entered and is not utilized in the diagram to follow. Such a diagram is presented in FIG. 10 with three stable states a–c and employing the nomenclature "L" representing the signal at line 370 and "H" representing the signal at line 374. When these signals are present, they are identified by a logic 1, in their absence, they are identified by a logic 0. It may be recalled that the signal "L" is produced by the actuation of either the reset count switch 26 or squelch switch 27, while the "H" signal is asserted in response to only the probe mounted squelch switch 27. As defined by the state diagram, the two Mealy outputs will be present only during certain state transitions. In FIG. 10, the three stable states, a–c, are represented, respectively, by labeled circles 430–432. Resting state a at circle 430 is one where there is no pulse signal present from either of the comparators 360 or 361 and thus an $\overline{L}\ \overline{H}/00$ condition obtains, and in the absence of some signal, as represented at transitional loop 434, that resting state a will remain. However, should a pulse commence, for example having been derived at lower threshold comparator 360, then as represented by transition arc 436, a transitional is made to state b represented at circle 431. The condition L $\overline{H}/00$, if continuing or recurring, will cause the maintenance of state b as represented by the transition loop 438. However, if the pulse output from comparator function 360 is provided without the presence of a signal output from level 2 comparator 361, then a transition represented by transition arc 440 occurs at the termination of the pulse with the corresponding output from the discriminator function of 1, 0. This condition then may be represented as $\overline{L}\,\overline{H}/10$ as labeled upon the arc 440. The circuit then will have returned to stable state a as represented at circle 430 and an output transition to 0,0. Where the signal under evaluation is crossing both the lower threshold of comparator 360 and the upper limit of comparator 361, a transition occurs for the condition LH/00 as represented by transition are 442. As represented by transitional loop 444, the resultant stable state c then ensues. Because the pulses under evaluation will exhibit falling edges, the conditions represented at transitional loops 446 and 448 for respective conditions L $\overline{H}$/00 and $\overline{L}$ H/00 are present. However, with the presence of the condition $\overline{L}\,\overline{H}$, then the transition represented by transition arc 450 obtains with the condition $\overline{L}\,\overline{H}$/01 and state a is entered as represented at circle 430.

The state diagram of FIG. 10 additionally shows other possible logic events and results therefrom. For example, the presence of the condition $\overline{L}$ H/00 in connection with state a will result in the transition represented by transition arc 452 providing a transition to state c. Similarly, the condition LH/00 occurring in state a will result in a transition to state c as represented at transition arc 454. Based on the foregoing, the implementation of the discriminator circuit 380 may take a variety forms depending upon the desire of the designer. For example, the diagram can be implemented by programming in conjunction with an electronically programmable logic device (EPLD), for example a type EPM5130 marketed by Altera Corporation of San Jose, Calif. Alternately, more simple circuits may be employed using conventional semi-conductor logic devices. A more detailed description of the circuit shown at 330 is provided in above-noted copending application for U.S. patent application Ser. No. 08/543,032.

In the employment of probe 20 to locate a sentinel node within a grouping of regional nodes, for example, at the axilla, the probe mounted switch 27 becomes quite valuable to the surgeon whose interest and vision is concentrated at the incision and tissue wherein which, for example, 10–30 lymph nodes may be located, only one of which will have collected a radiopharmaceutical. In general, the radiation count rate emanating from this sentinel node will be at substantially higher levels than that witnessed at the duct through which the pharmaceutical will have migrated. Once that high activity region is found, by successively actuating switch 27 to carry out a squelch procedure, the system will read a base count rate over a selected interval, for example 5 seconds. At the end of that sampling interval, the system then will establish a threshold above that base count of pre-elected statistical significance. As discussed in connection with FIG. 6, the scanning procedure starts with a squelch over normal tissue several inches from the region of node-caused high count activity. This provides maximum sensitivity. The probe 20 is then moved slowly across the region of the node being bracketed. The positions of the beginning of sound and the end of sound bracket the position of the sentinel node in one dimension. The probe 20 is then scanned along a path at right angles to the first scan. The beginning and end of the sound range are noted. This brackets the position of the sentinel node in the second direction. The sentinel node will be near the midpoints of these sound ranges. To increase the precision of localization, the probe is moved to the edge of the region of sound and squelched. The scans are repeated and the region of sound will be narrower. Again, the position of the sentinel node will be near the center of the regions of sound. Because the approximate inverse square law of radiation propagation obtains for a source such as that contained within the sentinel node, this squelching procedure of guidance may be carried out in three dimensions, for example, both transversely until the axis 92 is directly pointing to the node and along the axis 92 toward the node until the window 84 is essentially adjacent the sentinel node. That node then may be dissected for evaluation by pathology. It may be observed that the reduced forward surface area of crystal 112 is of a size and/or diameter somewhat commensurate with a typically encountered lymph node. Because of the right cylindrical shape of the probe 20, the axial orientation thereof with respect to the sentinel node is more apparent to the surgeon.

As described in connection with FIG. 1, an alternative arrangement for carrying out this three-dimensional guidance procedure with probe 20 involves the use of switches 52 and 53 in conjunction with the threshold timing type ranging device 48. With device 48, instead of actuating switch 27, the surgeon, working within the sterile field of the operating room, can increment the squelch threshold level upwardly by depressing switch 52. That level can be decremented by pushing switch 53. Through the utilization of piezoelectric switches as are employed in conjunction with probe 20, the threshold trim device 48 may be sterilized, thus enhancing its adaptability to use within the noted sterile field. Pushing either of switches 52 or 53 will derive a control input to console 12 corresponding with an initial actuation of squelch switch 71 followed by an actuation of an appropriate one of switches 73 or 74. The control system of console 12 will respond by incrementing the squelch threshold level upwardly an mount related to the last occurring conventionally developed squelch level as provided from switch 27 on probe 20. In general, the incrementation upwardly is a value corresponding with the interval of the base squelch count rate. The mount of incrementing upwardly is limited, however, such that when the upper limit is reached, the surgeon will be required to carry out a conventional squelching operation with switch 27 to permit restarting of the incrementation process at a new range. By holding down either of the switch components 52 or 53, the incrementation will be carried out as a succession of increments occurring at a rate slightly faster than once per second.

Figure 11:
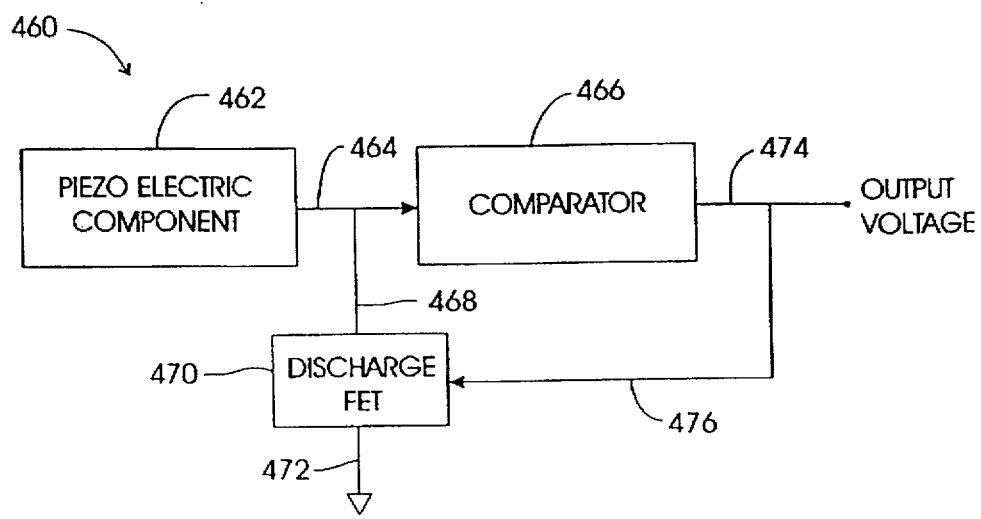
FIG. 11 is a block schematic diagram of a switching circuit employed with a threshold adjusting device shown in FIG. 1.

Threshold trim unit 48 as depicted in FIG. 1 includes two of the piezoelectric switches described in connection with switches 26 and 27 of probe 20. Additionally, the housing or enclosure 50 contains two identical circuits, one of which is shown in general at 460 in FIG. 11. Looking to that figure, the piezoelectric component such as that earlier described at 332 in FIG. 7 is represented at block 462. As before, this component 462 will include at least one resistor and a protective diode such as a Zener diode to protect devices downstream from voltage excursions occasioned, for example, with dropping component 48. The output of the piezoelectric component 462, when actuated, is presented as represented by a line 464 to a comparator network represented at block 466. Line 464 also is coupled as represented at line 468 with a discharge field effect transistor (FET) network as represented at block 470. Coupled to Found as represented at line 472, the gate component of the FET arrangement 470 is coupled with the output of comparator stage 466 as represented at lines 474 and 476. In general, in a quiescent state, the output of comparator stage 466 will be at supply voltage, for example, +12v, and this is asserted via line 476 to the noted gate of the FET of network 470. Any charge in the capacitive system represented at block 462 and within the network 470 is thus bled off. However, when the piezoelectric component is actuated, a rapid pulse-like charge build-up will be developed which will remain as long as the switch or piezoelectric component is depressed to compress the piezoelectric crystal. As a consequence, the voltage as ramped up can be retained by holding down the switch, for example, as long as 12 seconds. As the switch is released, a reversing charge occurs causing the voltage level to ramp down to a zero value. With the application of the switch on input to comparator stage 466, the discharge FET is disabled and a Found value will occur at line 474.

Figure 12:
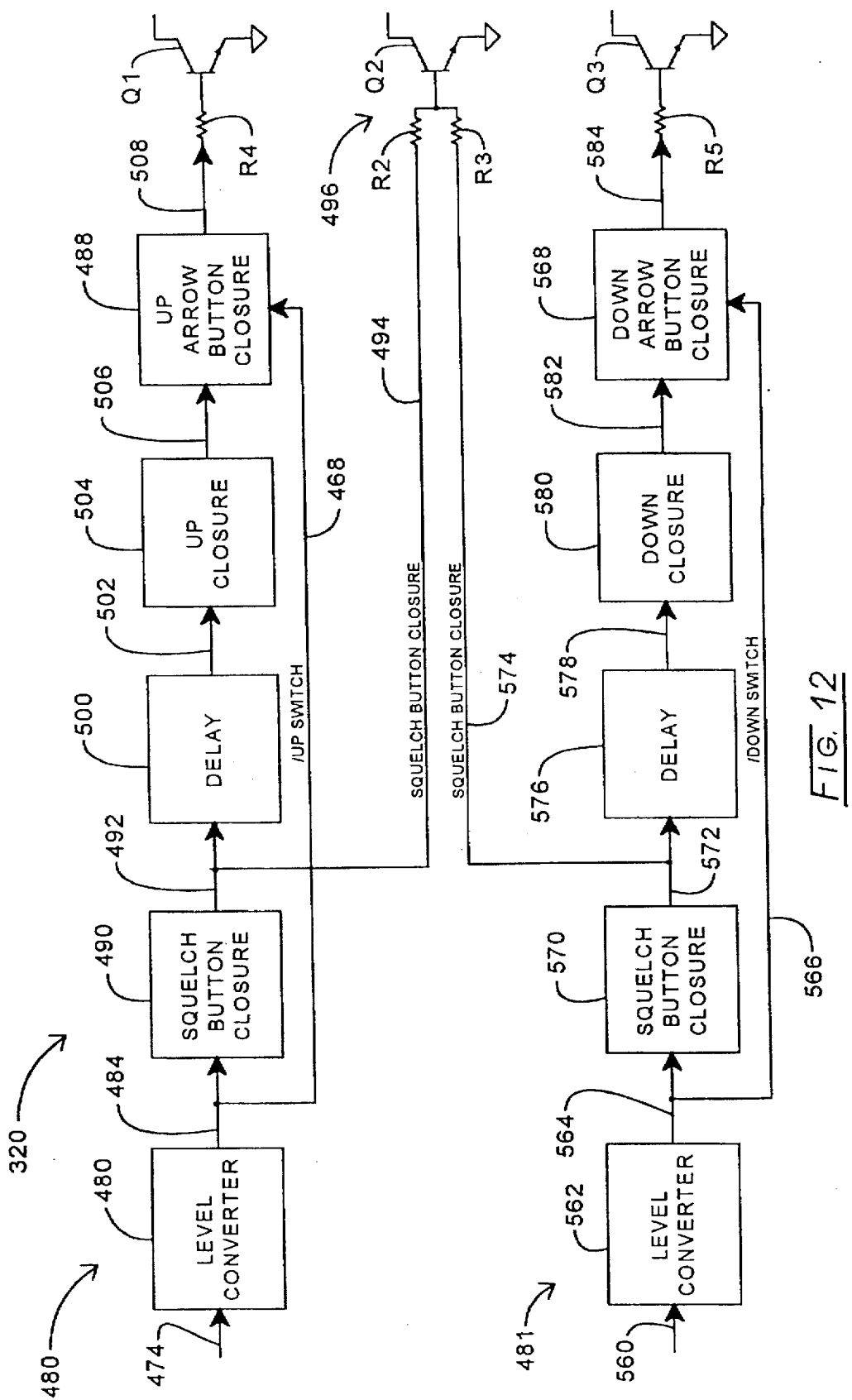
FIG. 12 is a block diagrammatic representation of a remote squelch trim logic function described in FIG. 5B.

Referring to FIG. 12, a circuit implementing the remote squelch trim logic discussed in connection with FIG. 5B and block 320 is illustrated in block diagrammatic form. Circuit 320 employs identical networks shown in general at 480 and 481 in connection with the inputs from each of the switches 52 and 53. Thus, these networks 480 and 487 are essentially identical, network 480 looking to an up switch actuation in response to the signal at earlier-described line 474 which is reproduced herein and a down switch closure, the output of which is represented at 560. The outputs of circuit 320 described at lines 322–324 in FIG. 5B are provided as open collector configured NPN transistors shown, respectively, at Q1–Q3. Transistors Q1 and Q3 are coupled across the low true corresponding outputs of respective up and down switches 73 and 74 of console 12. Transistor Q2 is similarly coupled across the output of squelch switch 71 of console 12. Looking initially to the up switch network 350, the input thereto from cable 46 and as described in conjunction with line 474 in FIG. 11 is presented again as leading to a level converter function represented at block 482. The network 482 converts the 12 volt level at line 474 to a 5 volt level and provides an improvement of that 5 volt level signal to achieve sharp transitions through the employment of a Schmitt inverter device. The output of the network 482 at line 484 will be a well formed pulse having a duration corresponding with the length of time that the surgeon has depressed switch 52. The signal at line 484 is designated as the variable "UP SWITCH" and is directed to line 486. Inasmuch as the signal at line 486 is a low true or negative true variety, it is identified with a slash mark.

The signal at line 484 also is directed to a squelch button closure network represented at block 490 which incorporates a timing device for generating an output pulse of predetermined fixed duration which is presented at output line 492 and additionally to line 494 for presentation through a resistive OR function 496 comprised of resistors R2 and R3, and for connection to the base of NPN transistor Q2 via line 498. Accordingly, with the presence of the squelch button closure signal at lines 492 and 494, transistor Q2 is mined on to emulate an actuation of squelch switch 71.

The signal at line 492 is coupled to the input of a delay network represented at block 500. This "delay" variable is interposed between the termination of the variable "squelch button closure" and the carrying out of an emulated actuation of UP switch 73. Following this delay imposed at the network 500, a signal is presented to an UP closure function as represented at line 502 and block 504. The UP closure network 504 develops a pulse of finite length selected to assure that the microprocessor-based system will recognize that a switching condition is at hand. The UP closure function 504 also provides an input as represented at line 506 to the earlier-described UP arrow button closure function 488. When the output at function 488 is true at line 508, transistor Q1 is mined on through resistor R4 for the duration of closure of the button switch 54.

Figure 13A:
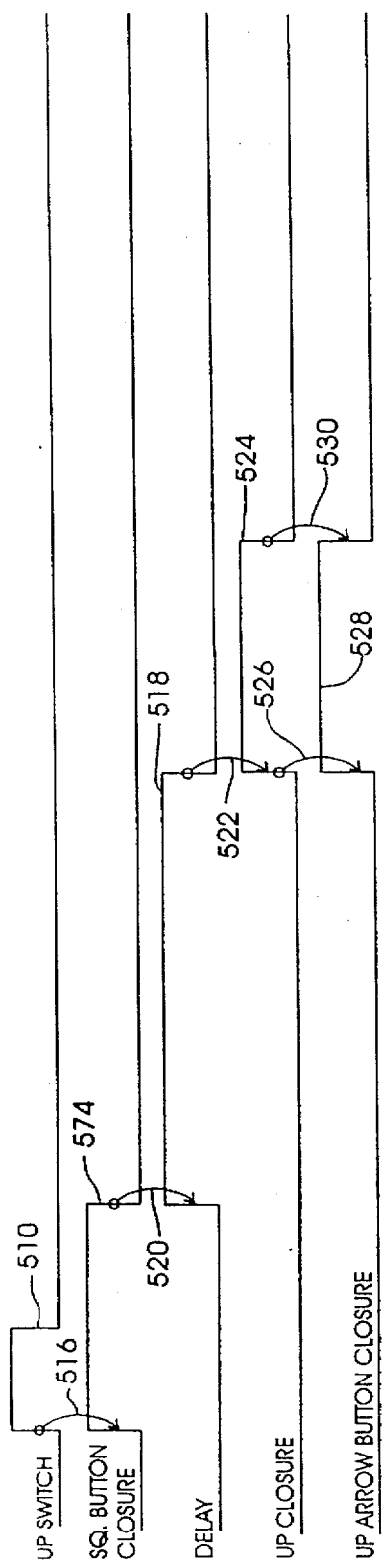
FIGS. 13A and 13B, respectively, show Boolean logic conditions for a normal switch actuation and an extended interval switch actuation with respect to the performance of the circuit of FIG. 12.
Figure 13B:
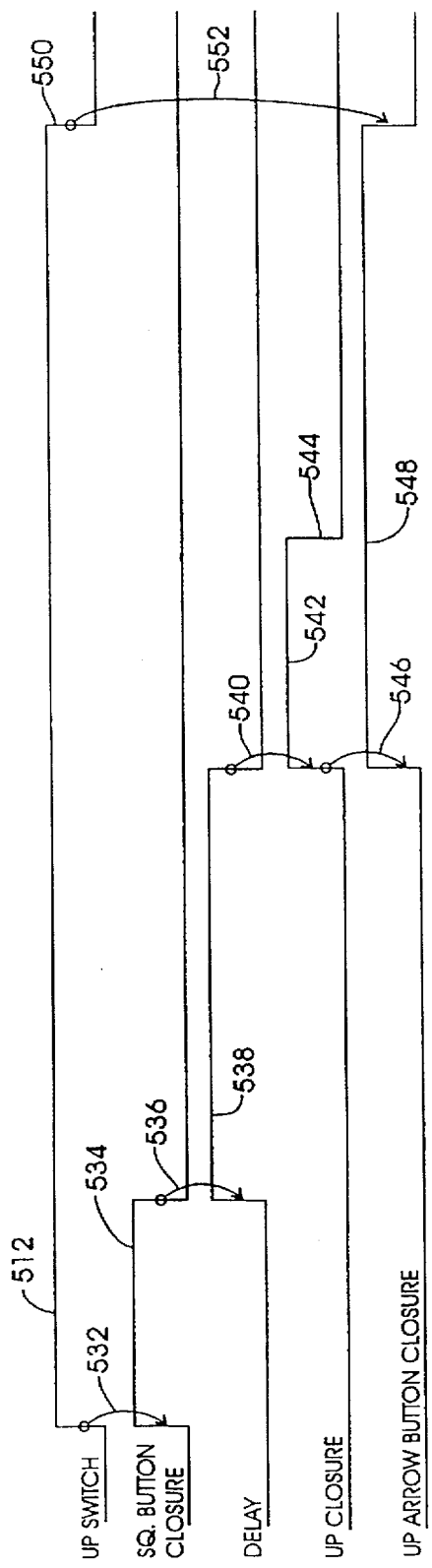

Looking momentarily to FIG. 13A, a timing diagram is presented showing the function of the variables associated with network 480 corresponding with the actuation of the UP switch button 52 on device 48. For the purpose of clarity, the variables in this diagram, as well as in the diagram of FIG. 13B, are represented in Boolean, 1,0 or true-false fashion, actual signals levels being ignored. The UP switch variable is herein represented as the pulse form 510. It will be true for an interval corresponding with the presence of pressure on switch 52. In FIG. 13A, a moderate or short interval of actuation of the switch is represented. FIG. 13B depicts the same variable in conjunction with an extended closure of switch 52 as represented by the pulse form 512. In FIG. 12A, the squelch button closure variable is represented in Boolean logic fashion as a corresponding one or true value at 514. This variable commences, as represented at transition arc 516, upon the rising edge or transition of the variable 510. The closure interval must be long enough to permit the microprocessor network 226 (FIG. 5B) to recognize a switch closure activity. A duration for this variable of about 100 milliseconds has been found to be adequate. It may be recalled that the logic represented at 514 is implemented at transistor Q2 from line 494. Upon termination of this variable, a delay is imposed as is represented at 518. The transition arc 520 shows that the variable at 518 commences with the falling edge or transition of the variable 514. The delay function 518 is interposed to assure that the microprocessor network 226 recognizes a sequence of closure of first the squelch function represented at switch 71 followed by the equivalent of an actuation of UP switch 73. Generally, this delay may be established as having a duration of about 200 milliseconds. As the variable 518 transitions to a logic zero from a logic 1, as represented at transition arc 522, the UP closure variable 524 becomes true. This UP closure variable will have a duration of about 100 milliseconds, an interval sufficient to assure that the microprocessor network 226 recognizes the switching condition. As the UP closure variable 524 transitions to a logic true condition, as represented at arc 526, the UP arrow button or switch closure variable becomes true or assumes a logic 1 condition, as is represented at 528. This logic condition, providing for the turning on of transistor Q1, for the short duration of UP switch variable 510, will have a duration commensurate with the UP closure variable 524, terminating as represented by transition arc 530.

Looking to the long duration presence of the UP switch variable as seen in FIG. 13B at 512, a logic providing for a correspondingly extended interval of the UP arrow button closure variable is developed. In the figure, as represented by transition are 532, the squelch button closure variable as represented at 534 commences in correspondence with the commencement of the variable 512. As before, this variable 534 will continue for an interval of about 100 milliseconds, whereupon, as represented by transition are 536, as the variable 534 transitions to a logic low or zero condition, then the delay variable as represented at 538 transitions to a logic 1 or true condition. As before, the delay will be of duration of about 200 milliseconds and at the termination of that interval, as represented by transition are 540, as the variable 538 transitions from a logic true or 1 condition to a logic zero condition, then the UP closure variable represented at 542 transitions to a logic true or 1 condition. As before, this variable will have a duration of about 100 milliseconds, whereupon it will transition to a logic zero state shown at the falling transition 544. The UP arrow button closure variable will transition to a logic true or 1 condition with the commencement of variable 542 as represented by arc 546.

This true condition, as represented at 548, however, will not alter its condition with the transition of variable 542 to a logic zero condition as represented at falling edge 544. The logic true or 1 condition 548 will persist until the transition of the UP switch variable 512 from a logic 1 or true condition to a logic 0 condition as represented at 550. The UP arrow button closure logic true condition will transition to a logic zero condition in correspondence with that activity at variable 550 as represented by are 552.

Returning to FIG. 12, network 481, performing in conjunction with the down arrow switch 53, is configured identically with network 480. In this regard, the network is shown having an input from the circuit associated with switch 53 at line 560. This input corresponds with that described at arrow 474 in connection with network 480. The input is filtered and its voltage level is convened in the same manner as provided in connection with function 482 as represented at block 562. A resultant level convened output is present at line 564 and delivers a down switch variable via line 566 to the down arrow button closure function represented at block 568. The function at block 568 is the down arrow equivalent of the network represented at 488 and discussed in connection with FIGS. 13A and 13B. The down switch signal at line 564 also is directed to a squelch button closure function as represented at block 570. This function is implemented in the same manner as network 490, providing a squelch button closure interval at its output at line 572 which is directed via line 574 to the resistive OR function resistor R3 and transistor Q2 via line 498. This same output is directed to a delay function represented at block 576 serving to provide the delay between the actuation of the squelch switch function and the down switch closure, a function corresponding with that at network 500. Following this inter-switch actuation delay, then as represented at line 578 and block 580, a down closure function ensues which is identical to the earlier-described UP closure activity described in connection with block 504. This down closure output is represented at line 582 extending to the down arrow button closure function as represented at block 568 and, as noted above, which corresponds to network 488. The output of function 568 is presented at line 584 which selectively provides a forward bias to transistor Q3 through resistor R5.

Another aspect of the present invention involves the method wherein system 10 is employed for the purpose of surveying or mapping the course of that lymph duct leading from a tumor or lesion to the sentinel node. The availability of system 10 for this method stems principally from a determination that the inverse square law of radiation propagatin does not obtain where radiation is emanating from a tubular confinement such as a blood vessel or lymph duct. In particular, the attenuation of radiation under those circumstances is at an inverse first power. This means, for example, that a lymph duct carrying $^{99m}$Tc may be mapped utilizing probe 20 and preferably in conjunction with computer 32. The inverse first power attenuation of radiation evidencing an activity per unit length of a duct is demonstrated in conjunction with FIG. 14. In developing the analysis associated with FIG. 14, an intuitive analogy to Guass's Law has been considered, to wit: if a source consisting of radioactive atoms is surrounded by an imaginary surface, and if there is no medium to absorb radiation, then all radiation must pass out through the surface regardless of the size or shape of the surface. Now consider a long cylindrical tube as at 590 with an activity concentration of N nCi/ml. If the radius, r, of the tube 590 is small compared to the half-value length for the radiation to be measured, the attentuation of radiation within the tube may be neglected. Since the direction of individual photons is random, the intensity of the radiation at a radius, R, from the center of tube 590 is not a function of position along the tube nor of angular position around the tube. All radiation passing through the surface of tube 590 also must pass outwardly through the concentric shell of radius, R, as shown at 592. The following calculations then may be considered per unit length of tube 590:

(1) volume of the unit length of tube $590=\pi r^2$;
(2) the area of a unit length of shell $592=2\pi R$;
(3) the number of photons through the unit length or section under consideration$=\pi r^2 N \cdot 37 \cdot k$, where k are the number of photons per disintegration and
37 is the number of disintegrations for 1 nanocurie $^{125}$I;
(4) the number of photons per unit area of shell 592:

$$= \frac{\pi r^2 N \cdot 37 \cdot k}{2\pi R} = \frac{37 k N r^2}{2R}$$

From the foregoing, it may be noted that them is no squared term in the denominator of expression number 4.

If a detector having a forward surface area, A, is placed at a distance, R, such that A is much smaller than $2\pi R$, then the number of photons per second detected for the above-noted $^{125}$I source will be:

(5)

$$\frac{37 k N r^2 A \eta}{2P};$$

where $\eta$ is equal to detector efficiency.

Figure 14:
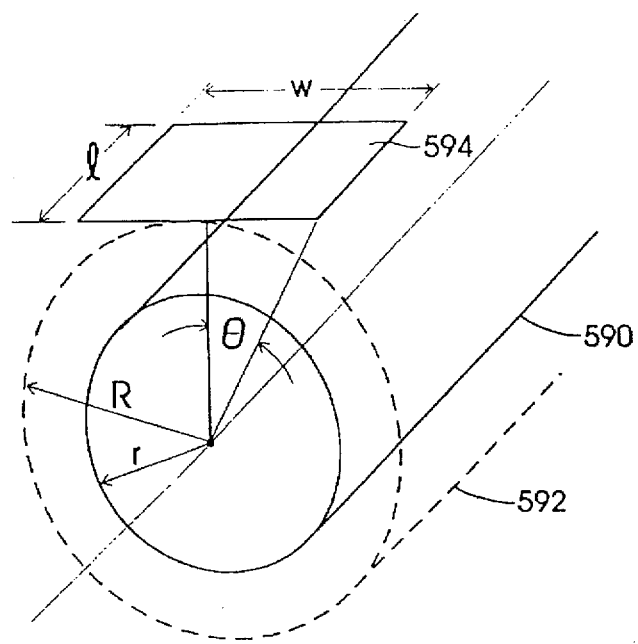
FIG. 14 is a perspective representation of a duct which is utilized in evaluating the emanation of radiation from a lymph duct.

For a rectangular detector placed relatively close to the duct or cylinder 590 as shown at 594 in FIG. 14, the area is projected onto the cylinder shell 592. With this geometry, the number of photons per second detected may be computed as follows:

(6) A=lw
(7) A=2l tan θ
(8) projected area=2lRθ
(9)

$$\text{photons/second detected} = \frac{37 k N r^2 A \theta \eta}{2R \tan \theta}$$

where, $$\tan\theta = \frac{w}{2R}$$

(10) photon/second detected=$37kNr^2 l\theta\eta$.

Figure 15:
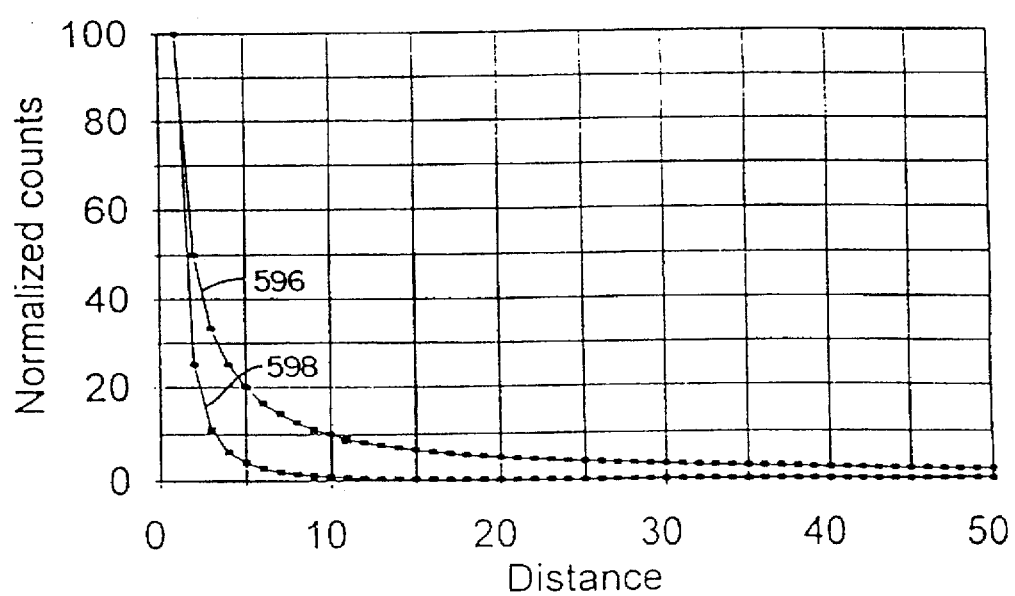
FIG. 15 is a chart showing normalized counts with respect to distance from radiation propagation according to the inverse square law and in accordance with the first power.

The advantage accruing from this first power decay of radiation which is manifested in the mapping of radiopharmaceuticals migrating within a lymph duct is demonstrated in FIG. 15. Here a curve 596 is presented relating normalized count rate levels with arbitrary distance such as millimeters. Plotted along with curve 596 is a curve 598 representing the long recognized inverse square law of decay. It may be observed that curve 598 falls very rapidly and sharply to very low values. By contrast, the inverse first power relationship of curve 596 representing count rates from a duct or cylinder 590 shows a much more gradual fall-off with distance. As a consequence, a mapping approach to tracing radiopharmaceuticals as they migrate from a lesion or tumor to a sentinel node becomes a realistic diagnostic modality. To carry out such mapping, the probe 20 is moved along the epidermis or skin with the probe axis 92 generally being retained in an orientation perpendicular to the skin surface, particularly over the location detected for the duct. Another important aspect of developing a dynamic plot or graphics representation from which duct position can be located resides in the development of sharp radiation count peaks when the probe 20 axis 92 is substantially radially aligned with the duct, i.e. an alignment with radius, R. Where such sharp peaks are dynamically plotted, the clinician is readily able to visualize lymph duct location. Where probe 20 is used in the manner noted, the probe 20 axis 92 initially is oriented in a manner defining a scanning surface at a location adjacent the epidermis under which the lymph duct is located. Then the probe 20 is moved outwardly and transversely and returns while maintaining the detector forward surface in parallel relationship with the scanning surface.

Figure 16:
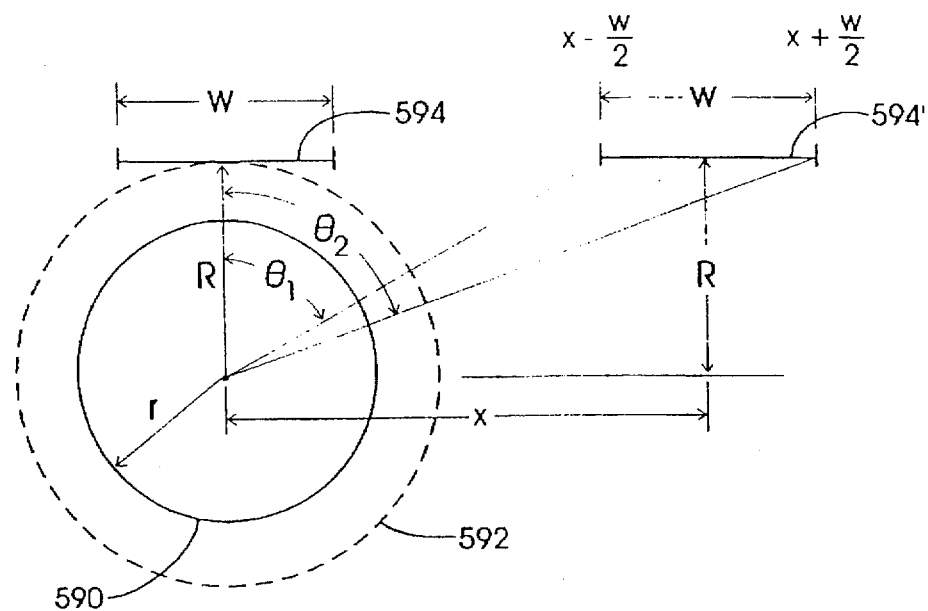
FIG. 16 is a sketch employed in analyzing the fall-off effect of moving a crystal detector away from a duct carrying a radiation source.

Looking to FIG. 16, the peak development with such surveying or scanning can be evaluated. In the figure, the forward detector surface 594 initially is positioned as represented in FIG. 14. Then, however, the detector surface is moved transversely toward the location shown in the figure at the common radius height, R, but at a distance, x, spaced from the center of duct 590. Considering the projections of radiation from the center of duct 590, the leftward edge of detector 594' is located at the transverse distance, x–w/2, at a projection from perpendicular of angle $\theta_1$, while the opposite outwardly disposed edge thereof is located at a transverse position x+w/2, and at a corresponding angle $\theta_2$. The geometry of this arrangement may be considered as follows:

(11)
$$\tan\theta_1 = \frac{x - \frac{w}{2}}{R}$$

(12)
$$\tan\theta_2 = \frac{x + \frac{w}{2}}{R}$$

(13) w=R(tan $\theta_2$–tan $\theta_1$)

(14) R($\theta_2$–$\theta_1$)=the projection of width w on a cylinder of radius, R.

(15)
$$\text{the detected photons per second} = \frac{37kNr^2 A\eta}{2R} \cdot \frac{\theta_2 - \theta_1}{\tan\theta_2 - \tan\theta_1} = \frac{37kNA\eta(\theta_2 - \theta_1)}{2\pi w}$$

The above derivations can be plotted with respect to a theoretical duct carrying 5.39 microcuries of total activity. Looking to FIG. 17, such a plot is revealed. In the figure, the theoretical detector surface is moved transversely a distance from the center of duct 590 ten cm to either side in the manner of FIG. 16. The computations resulting show plots 600–605 for respective vertical distances above the center of the duct of 10 mm, 12 mm, 17 mm, 22 mm, 27 mm, and 32 mm. As may be expected, as the distances away from the duct 590 increase in a vertical sense, then the curves tend to flatten and peaks are lost. However, at distances such as 10 mm and 12 mm as shown at curves 600 and 601, respectively, very definitive peaks are realized.

Figure 17:
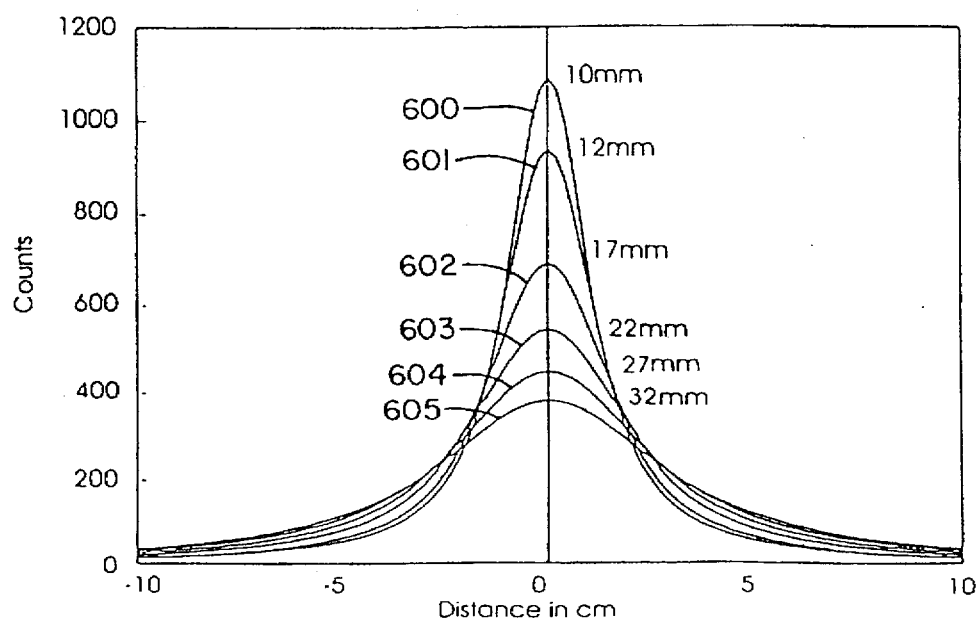
FIG. 17 shows a theoretical study wherein a crystal detector surface is moved transversely a distance from the center of a radiation duct at varying heights thereabove.
Figure 18:
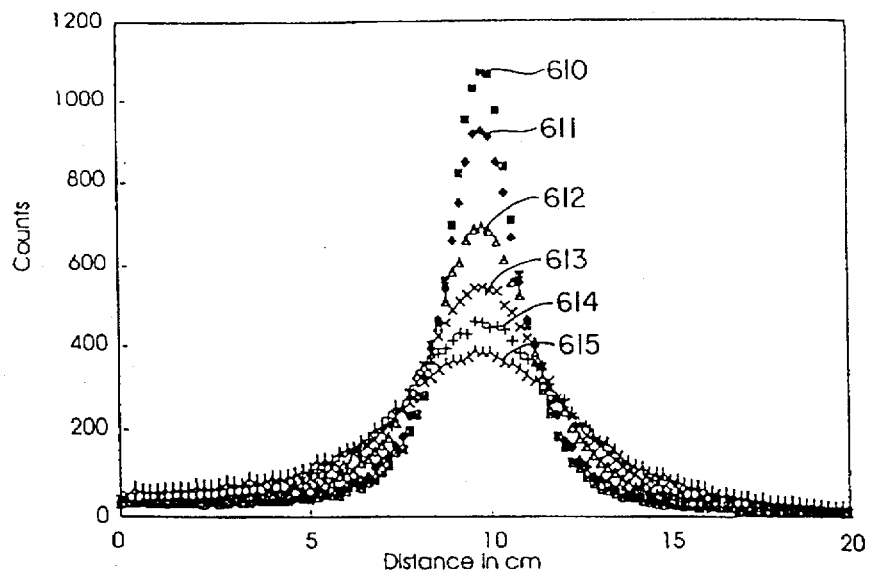
FIG. 18 is a compilation of plots taken by experiment wherein a crystal detector is moved vertically and transversely with respect to radiation contained within a plastic duct.

The theoretical study of FIG. 17 was verified with an experimental duct model. In this regard, a rigid polymeric tube having an outer diameter of 1.6 cm and an internal diameter of 1.38 cm, and an overall length of 19.8 mm was carefully filled and capped with 11.0 microcuries of $^{125}$I in fluid solution. Commencing at the surface of the tube, then a conventional probe as described in U.S. Pat. No. 5,070,878 by Denen, issued Dec. 10, 1991, was moved in a scanning motion in a geometric manner as described in connection with FIG. 17 commencing at the tube transversely scanning at surface level and then at upwardly disposed elevations from the tube for a sequence of runs. The results then were plotted in the manner of the plots of FIG. 17, the probe, now having a round as opposed to rectangular surface periphery being moved a distance of 10 cm transversely outwardly in either direction from the center of the tube carrying $^{125}$I. The resultant plots are shown in FIG. 18 at 610–615 representing distances from the outer surface of the tube, respectively of 0 mm, 4 mm, 6 mm, 10 mm, and 20 mm. Comparing the pattern of plots 510–615 with the computed plots at 600–605 of FIG. 17 shows a substantial similarity confirming the ideal conditions of count peaking from the detector surfaces radially aligned with the duct under investigation and which carries a radiopharmaceutical or the like.

Figure 19:
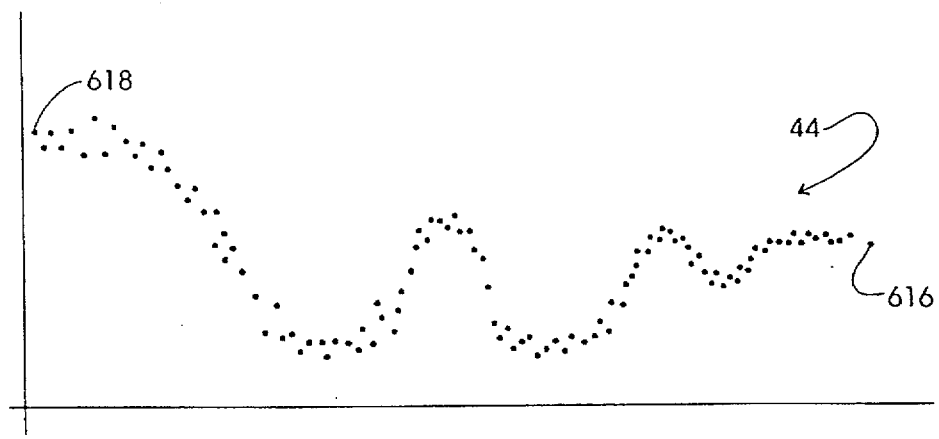
FIG. 19 is an enlarged view of the visually perceptible output shown in FIG. 1.
Figure 20:
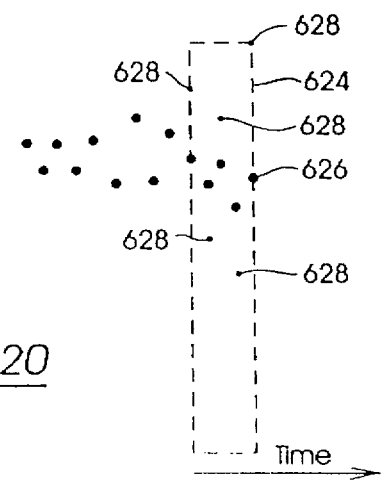
FIG. 20 provides a schematic illustration of carrying out a moving average filtering function.

The dynamic graphical mapping of the count outputs of probe 20 as it is manipulated to locate a radiopharmaceutical carrying lymph duct is represented again in FIG. 19 at 44. The dots or pixels representing the dynamic curve shown at 44 are the product of appropriate read and write operations preferably to a circularly accessed data memory. Specifically, a new averaged data value is written to this dedicated memory every 0.1 second. Specialized read and write access to this memory causes the curve to scroll from the right to the left side of the display. With such scrolling, the dot at 616 is the most recent data and the dot at 614 is the oldest data being, for example, about 20 seconds old. Thus, as the practitioner maneuvers probe 20 across the lymph duct over the skin of the patient, peaks readily are discerned representing approximately an orientation wherein the axis 92 of probe 20 is pointing at the radiopharmaceutical containing duct. However, each of the dots as extending from 616 to 618 represents a noted weighted average and, for example, will have taken one-half second to generate. Each of the dots as at 616 and extending to the oldest at 618 may be generated as an average or sum of shorter interval samples. For example, the system is employed using samples taken over 1/10th second intervals and these 1/10th second interval samples are continuously averaged within a half second interval or window of time. Thus, the display of ½ second interval data is updated every 1/10th second. This impulse filtering arrangement is represented in FIG. 20 in conjunction with a dynamic time window shown as a dashed rectangle 624. With this representation, the most recently produced dot as described above at 616 and here shown at 626 is the average of 1/10th second count samples for the next previously developed half second of window 624. These 1/10th second samples are represented by smaller dots 628. It may be observed from FIG. 20 that if only the 1/10th sample intervals were employed, more difficulty would be experienced in locating the peaks. This situation obtains principally because of the very random nature of photon emissions. It also becomes apparent from FIG. 20 that any given dot, for example that at 616 shown in FIG. 19, will represent a sampling delay such that the probe 20 will be slightly displaced with respect to the values that are represented by it. By looking to a graphics representation, it is easier for the practitioner to visualize the appropriate location of the duct with respect to the probe axis 92.

Figure 21:
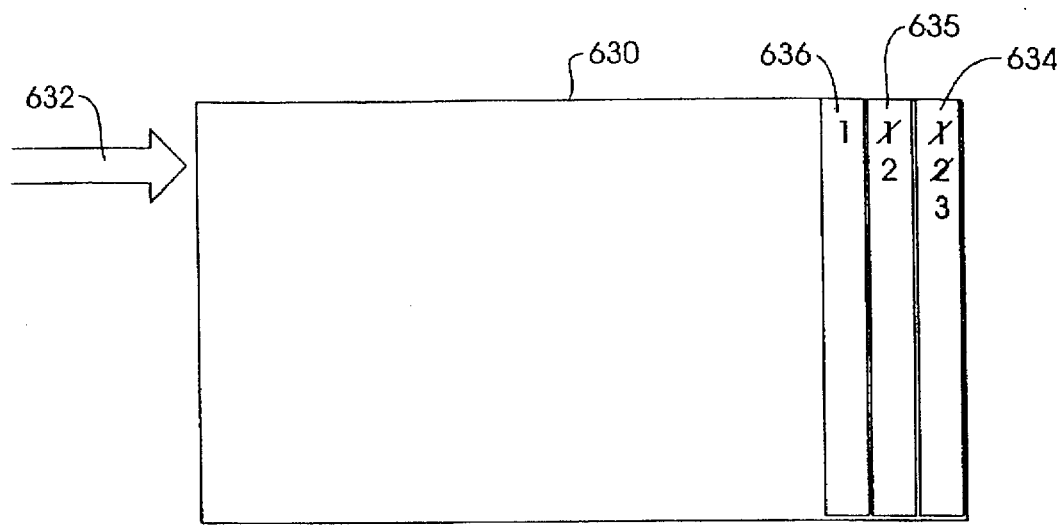
FIG. 21 is a schematic illustration of a memory employment which may be utilized to generate the visual output of FIG. 19.
Figure 22:
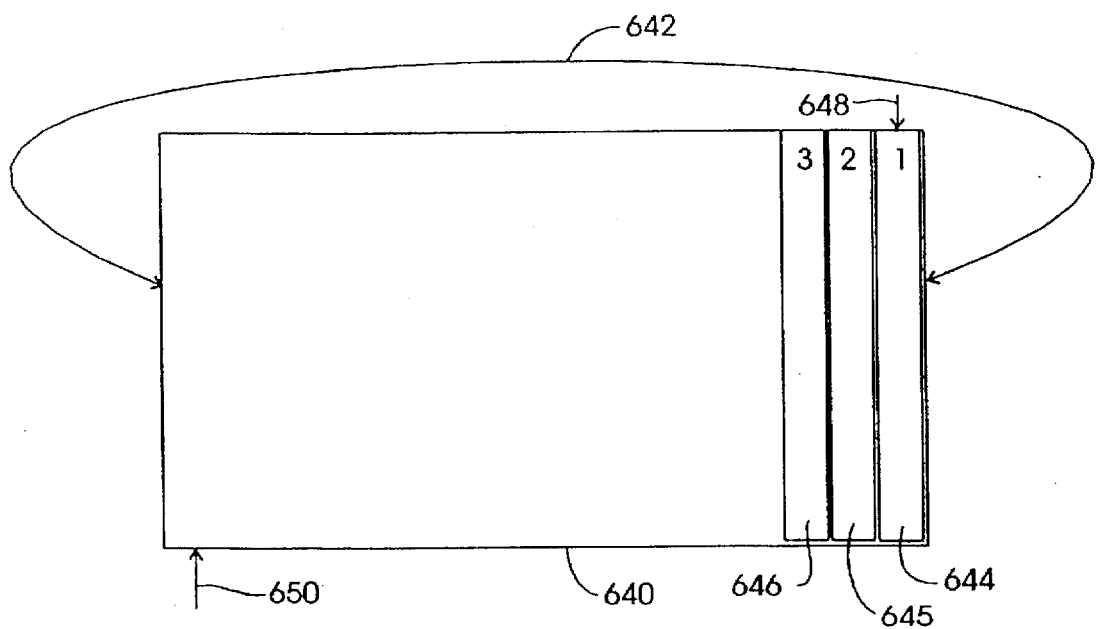
FIG. 22 is a schematic illustration demonstrating a dedicated circular memory arrangement as an alternative to that described in connection with FIG. 21.

The technique employed for carrying out the right-to-left scolling at display 44 will depend upon the computer implementation at hand. For a conventional personal computer as at 32, the technique for scrolling will depend upon the constraints of its operating system. In general, where the scrolling feature is developed for conventional operating systems, each of the dots displayed at the screen within the array 44 is within a predesignated columnar location and each such columnar location also is provided in conjunction with a location in computer memory. The memory-based operation for the PC operating system approach is illustrated schematically in FIG. 21 in conjunction with a block 630 which may represent memory. This memory 630 typically is addressed in repetitive sequential order from right-to-left by an address function represented at arrow 632. In general, a sequence of address assignable locations in memory 630 are designated to receive one of the 0.5 second count averages, for example the first three of such regions are represented in the boxes 634–636. Assuming the data commences to be collected, then the first component of data indicated by a "1" is submitted to memory location 634. Correspondingly, ½oth second later, the second memory component occurs and is overwritten in block 634, while the initial data component earlier designated 1 now is rewritten in next memory position 635. This is represented by adding a 2 to block 634 and a / through the numeral 1. The third increment of a half second data then is written into block 634 over that earlier presented as 2 and that second data collection is written in memory position 635 over the earlier-presented first period. Meanwhile, the initial data identified as "1" in memory position 635 is rewritten at the next adjacent memory position 636. Thus, the expunged or overwritten data is shown in blocks 634–636 as being crossed out with a / mark. As is apparent, while scrolling performance is achieved with this conventional approach, it is inefficient.

Where a dedicated memory, for example associated with the LCD readout of console 12 is available, then that dedicated memory can be employed as a circular memory with more efficient software utilization. Looking to FIG. 22, a memory component again is represented by a block as at 640 and the circular functioning of the memory is schematically depicted by the loop 642. Three memory positions again are represented within block 640 by boxes 644–646 and data in a sequence of 1–3 as shown written, respectively, in these boxes. This data will continue to be written to the end of memory in conjunction with a write pointer represented at arrow 648. Correspondingly, a read pointer is designated as represented at 650. The read pointer is incremented from left to right, while the write pointer 648 positions data in memory in the sense of fight to left. Both pointers wrap around as represented by loop 642. To achieve a scrolling, however, the phasing of the read pointer is changed incrementally with each read entirely through the memory block 640. In effect, all of the data is translated to the left by a given increment and the oldest data is dropped out of memory by being written over. Generally, a variety of techniques are available to the designer for avoiding a conflict of reading and writing at the same memory location.

Figure 23:
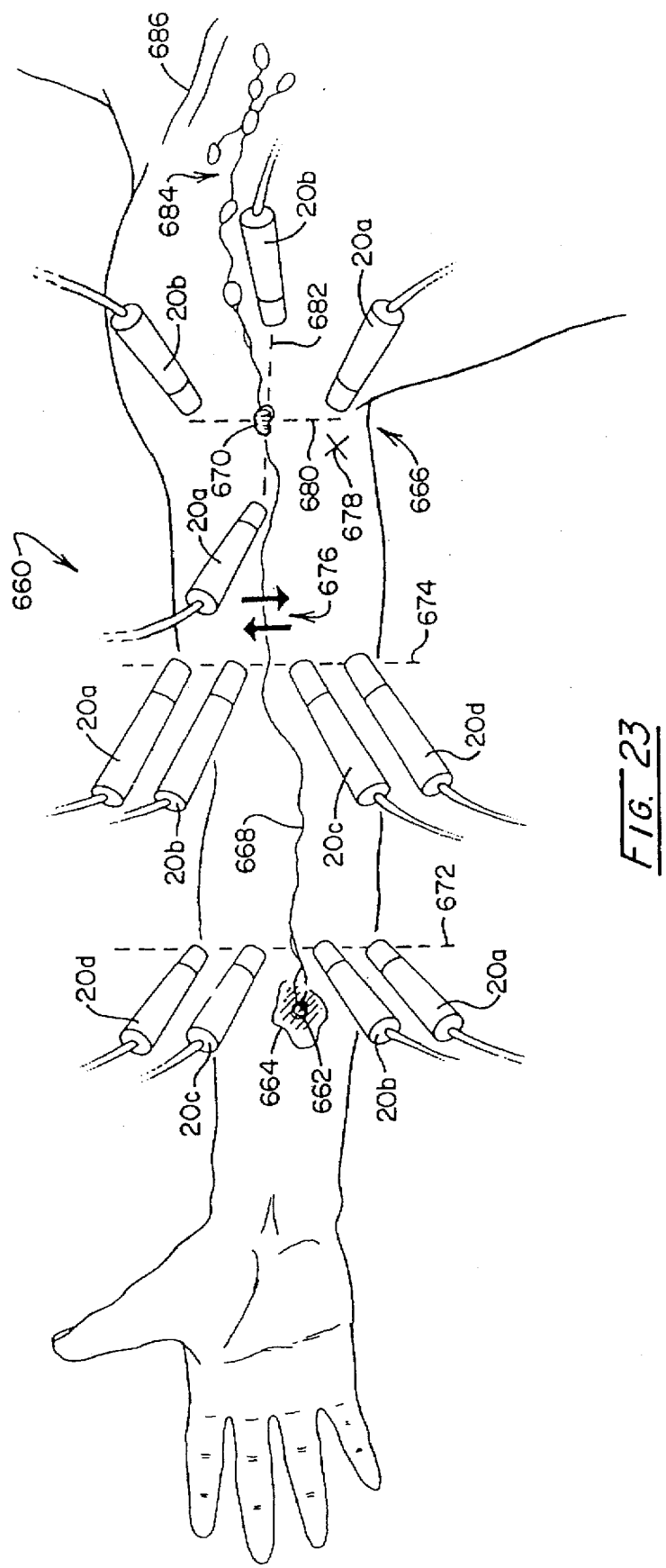
FIG. 23 is a view of the anterior aspect of the right upper limb showing the position of a cutaneous melanoma, lymph duct, sentinel node, clavical, and semi-clavicular nodes.

Now looking to the utilization of system 10 in tracking the migration of an injected radiopharmaceutical, reference is made to FIG. 23 where an upper fight limb is illustrated from an anterior aspect as represented generally at 660. Depicted upon the forearm is a cutaneous melanoma shown as a dark dot-like region 662. This lesion 662 is readily identified visually by the practitioner and with the procedure, a radiopharmaceutical is preferably injected in four quadrants or in quadrature about the lesion 662. While any of a variety of radiopharmaceuticals may be employed for the instant purpose, a preferred one is a sulfur colloid labeled with $^{99m}$Tc. As noted above, this particular radiopharmaceutical is of relatively low cost, is readily available in the marketplace, and represents an approved pharmaceutical product. Another advantage associated with its use resides in its short half-life (6 hours) which results in its being essentially gone from the body of the patient about three days following injection. The resultant injection of radiopharmaceutical in quadrature will create an area of high count rate or count intensity immediately surrounding the lesion 662. Typically, the boundary of this region of high activity may be represented as shown by the lobed outline 664. For the instant illustration, the practitioner will know that drainage will occur toward a sentinel node located somewhere at the axilla represented generally at 666. Fortuitously, the injected radiopharmaceutical will migrate along a lymph duct as represented at 668 toward an initial, sentinel node located somewhere in the axilla 666 and here represented at 670. To track this migration, the probe 20 is employed in conjunction with the graphics display 44 in a sequence of transverse scanning motions which are carried out to take advantage of the sharp peak development achieved by manipulating probe 20 in the manner discussed above in connection with FIGS. 16 through 18. In this regard, a transverse locus is represented at dashed line 672. The probe 20 may be maneuvered, for example, as represented by the sequential positions 20a–20d while the practitioner observes a readout as illustrated at 44 in FIG. 19. The position of the probe 20 as it passes across the duct 668 will be established by observing peak levels of the curves at readout 44, it being understood that a very slight delay will be recognized in consequence of the queueing and averaging being carried out by the microprocessor based control system. As the peaks are recognized in conjunction with the location of the probe 20, the practitioner may, for example, place a small ink dot on the epidermis above the thus-located lymph duct. While the probe representations 20a–20d are shown slightly canted for the purpose of clarity in the drawing, the preferred orientation of the probe is in a scanning plane such that the axis of the detector earlier-described at 92 has the orientations described in conjunction with FIG. 16, the forward surface of the detector being in somewhat parallel relationship with the scanning surface. Other scans may be carried out, for example, at a further distance from the lesion 662 as shown by the locus represented by dashed line 674. Here, again, the probe may be moved in a scanning motion along such locus as represented by the progressive probe positions 20a–20d, the particular direction for this illustration being opposite that shown for the scan at locus 672. Other scans may be carried out in either direction across the upper limb from an anterior aspect as represented by the paired arrows 676. Definition of the peaks particularly is achieved by virtue of the observation described above in conjunction with FIGS. 14 and 15 that attenuation of radiation from the duct 668 is at a first power as opposed to a second power. However, as this tracking procedure approaches the sentinel node 670, a substantial increase in count rate activity will be witnessed inasmuch as the node 670 will have accumulated radiopharmaceutical. It thus exhibits the characteristics of a radiation point source where radiation attenuation is in accordance with the inverse square law of radiation propagation. At this juncture, then a different approach in the employment of the probe 20 is used. For this activity, the probe 20 becomes a guide leading the user to the sentinel node 670 through the utilization of the earlier-described squelching procedure which may be employed utilizing the button switch 27 and a count rate threshold adjustment using device 48. Upon encountering the substantially rapid increase in radiation count rate in the vicinity of sentinal node 670, the first procedure undertaken is that of establishing a base count rate at a location at the periphery of the radiation activity emanating from node 670. For example, the probe 20 maybe located at the point marked by an, "x" 678, whereupon the squelch button 27 is depressed and a base threshold count rate is established over an interval of 5 seconds. Upon the development of this base count rate, then a bracketing traverse is carried out across the area of activity during which the practitioner listens for the development of the "siren" aural output from control console 12. In this regard, the probe 20 may be moved along a first locus such as that represented at dashed line 680 from location 20a to location 20b. As the probe 20 passes over the sentinel node 670, a substantial increase in sound output frequency will be heard and the location bracketed by that aural output may be observed in the manner discussed in connection with FIG. 6 above. A scan along a transverse locus represented by dashed line 682 then may be carried out, for example, as represented by a movement of the probe along locus 682 from the location shown at 20a to that shown at 20b. Then, for example utilizing switch 52 of device 48, the count rate threshold may be raised and again the boundaries of aural output are developed in a bracketing procedure as described in connection with FIG. 6. As the location directly above the sentinel node 670 is determined, then a small incision may be made and the same procedure is carried out through the incision toward the node 670 until it is bracketed to an extent wherein the axis 92 is pointing directly at it and the forward surface as at 84 of the probe 20 is essentially in adjacency with node 670. Thus, the node 670 is distinguished or differentiated and identified singularly from other adjacent regional nodes such as the subclavicular nodes represented at 684 which approach the clavical represented at 686. Of course, other axillary nodes are present the basin region surrounding node 670. Upon removal of the node 670, it is submitted to evaluation by a pathologist to determine the presence or absence of metastasis. As noted above, the squelching switch 27 may be used exclusively for this bracketing procedure. However, that procedure requires a five second count interval. A more swift adjustment of the threshold accordingly is available through the utilization of the device 48. However, as noted above, there are limitations to the available alterations or range of the threshold level. Where such a range limit is reached, then another squelching procedure is carried out to re-establish a base count rate.

Figure 24:
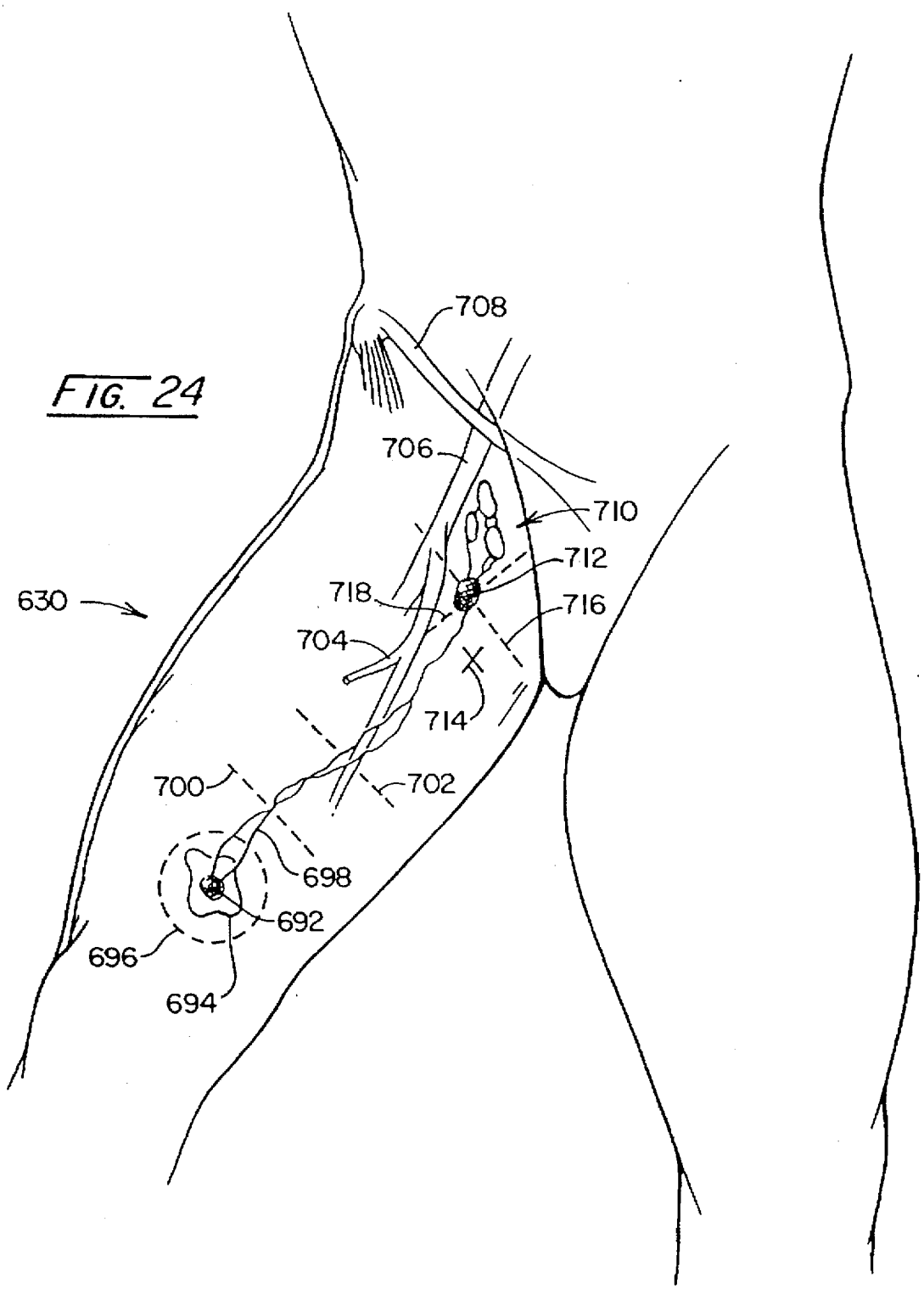
FIG. 24 is an anteromedial aspect view of the lower limbs showing lymphatic drainage from a cutaneous melanoma toward regional superficial inguinial nodes.

Referring to FIG. 24, an illustration of the fight lower limb from an anteromedial aspect is revealed in general at 690. Located upon the right thigh above the kneecap is a cutaneous melanoma depicted at 692. Again following in the procedure described above in connection with FIG. 23, injection of radiopharmaceutical is made in quadrature about the lesion 692 which readily is visually discerned and identified by the practitioner. This results in a region of high count rate activity surrounding the lesion 692 as represented by the lobed boundary 694. The practitioner next determines which lymph duct is carrying the radiopharmaceutical following the relatively short interval required for it to migrate into a given duct or ducts. For this purpose, the probe 20 is moved along a locus surrounding and spaced from the site of the neoplastic tissue 692 as represented by the circular dashed line 696. By observing the graphics readout 44, as the probe 20 passes over a lymph duct carrying migrated radiopharmaceutical, a peak will be observed in the graphics display to identify the duct of conveyance. Such a lymph duct is shown in FIG. 24 at 698. Upon determining the location of that duct which is carrying radiopharmaceutical, then the procedure described above in connection with locii 672 and 674 is carried out as duct 698 is located by peak graphics observations. Two traversing locii along the groin are shown at 700 and 702. As before, upon observation of a peak at the graphics readout 44, a mental note as to probe location may be made by the practitioner or a small ink dot may be positioned upon the epidermis as the radiopharmaceutical carrying duct is, in effect, mapped or surveyed. Duct 698 is seen passing the greater saphenous vein 704 extending from the femoral vein 706 above which the inguinal ligament 708 may be observed. The sentinel node to which duct 698 extends is shown as a node 712 within regional nodes which generally are identified as superficial inguinal nodes represented generally in the region 710. As the sentinel node, now carrying a substantial amount concentration of radiopharmaceutical and shown at 712 is encountered, the readout 44 will evidence a sharp increase in count rate activity and the second aspect of the detection and removal procedure then ensues. A squelching or base count rate derivation procedure is carried out at the periphery of this region of enhanced count rate activity, for example at the location "x" shown at 714. This may be accomplished either by actuating button switch 27 or carrying out the procedure of actuating switch 71 followed by the actuation of switch 70 on console 12. As noted above, generally a five second counting interval is undertaken by the system upon such actuation. Upon thus establishing a base count rate, the practitioner then carries out an initial bracketing across the region of high activity representing the location of sentinel node 712. Such traversing locii are shown in the figure at 716 and 718. Utilizing procedures described in conjunction with FIG. 6 above, the sentinal node 712 readily is bracketed initially above the epidermis of the patient whereupon a small incision is made and the procedure continues utilizing, for example, switch 52 to increase the count rate threshold as movement of the probe 20 utilizing the aural or "siren" output brackets location of node 712 both traversely and along the equivalent of a z axis. It is desirable that the ending and differentiating location of the probe 20 is one wherein sound is still heard over a very short movement such that the clinician is assured that the system is properly reacting. As noted above, there are limitations in the system for advancing the threshold count rate utilizing, for example switch 57 of device 48. Where the limits of the system are reached, then another squelching procedure is required, for example, through actuation of switch 27 on the probe 20.

Figure 25:
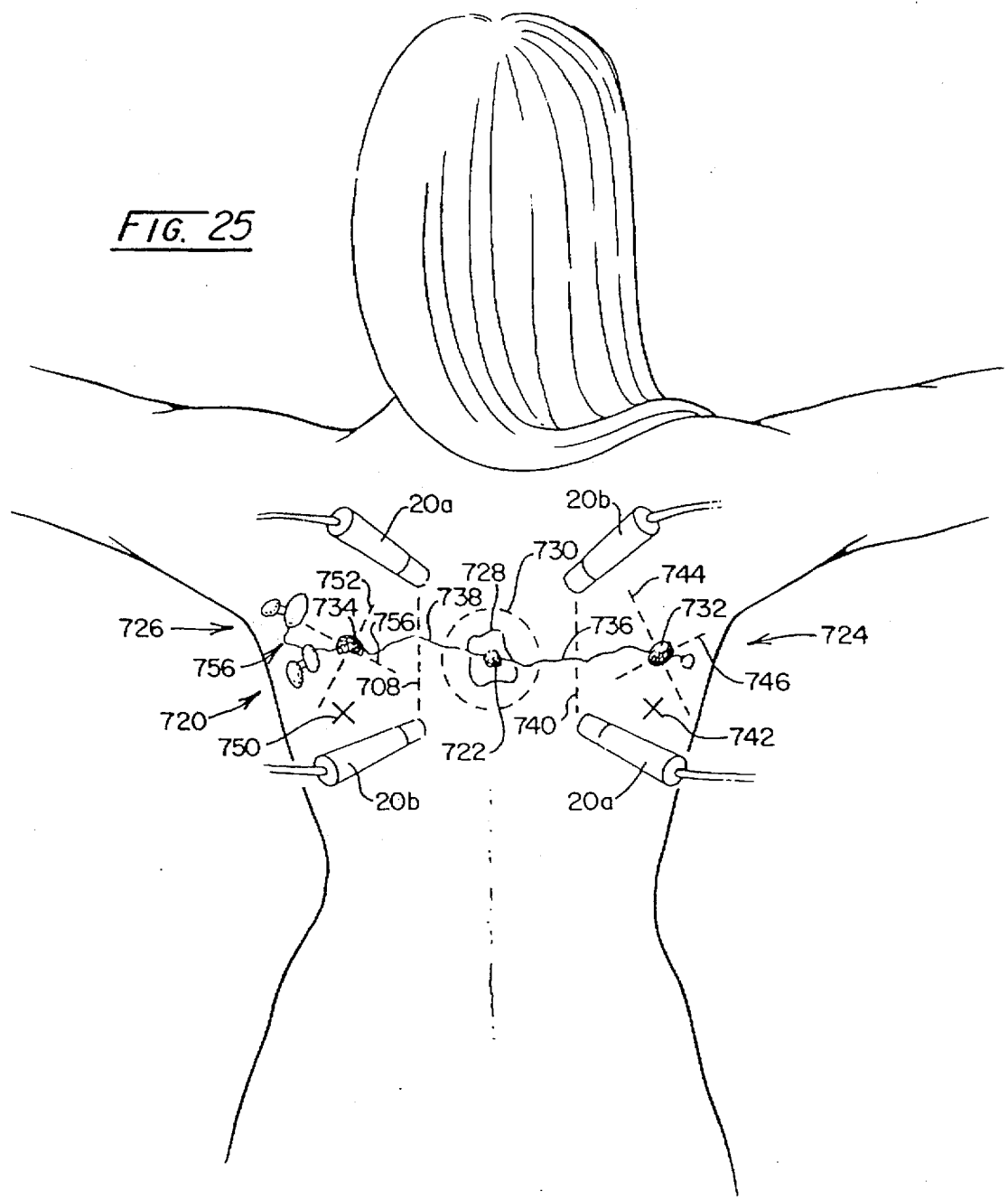
FIG. 25 is a posterior view of the upper torso showing medially located cutaneous melanoma and dual branching lymph duct drainage.

Looking to FIG. 25, the upper back region of a patient is represented generally at 720, medially upon which there is located a cutaneous melanoma 722. In some cases, the practitioner will find that radiopharmaceutical drainage extends to the auxiliary lymph node basin or region associated with both the fight and the left limb as represented, respectively, in general at 724 and 726. A radiopharmaceutical is injected in quadrature at the location of the lesion 722 which will result in a region of higher count rate activity shown by the lobed boundary 728. Upon permitting a passage of time adequate for migration of the radiopharmaceutical along a lymph duct leading to a sentinal node, the probe 20 is moved in a locus surrounding and spaced from the activity region boundary 728, for example along the circular locus shown by dashed line 730. Assuming that two sentinel nodes are present as shown, for example at 732 and 734, then a peak visual output will be seen at display 44 as the lymph duct 736 is encountered and additionally as the lymph duct 738 is encountered. Accordingly, each of the ducts 736 and 738 are mapped or surveyed in the manner disclosed above. For example, with respect to duct 736, transverse scans or traverses are made as represented by the locus shown as a dashed line 740. The duct 736 is mapped by carrying out a traverse thereacross using the probe 20, for example from the location shown at 20a to that shown at 20b while observing readout 44. The probe representations at 20a and 20b are slightly angularly oriented with respect to the desired traverse orientation where detector axis 92 is perpendicular to the scanning surface at the epidermis of the patient. This is in the interest of a clearer illustration. As the duct 736 is mapped by the noted traverse in conjunction with observation of peak count rate development at display 44, ultimately, the region wherein sentinel node 732 is located will be determined because of a substantial enhancement of count rate activity. At such time, the probe 20 is located at the periphery of this enhanced activity region and a squelching or base count rate establishment procedure is carried out, for example, by actuating switch 27 or switches 71 and 70 in sequence. The location, for example, for such a base count rate threshold determination is shown by an "x" at 742. Following this base count rate threshold development, the region of high activity is traversed, preferably in two transverse directions, such transverse locii being represented by dashed lines 744 and 746. Bracketing procedures then are carried out as described in connection with FIG. 6 above until the probe 20 is located directly over sentinel node 732. At this juncture, a small incision is made and the procedure continues as described above, for example employing switch 52 of device 48 until the forward surface of probe 20 is substantially adjacent sentinel node 732 and the axis thereof at 92 is pointing directly at the node. Sentinel node 732 then is removed for evaluation as to the presence or absence of metastasis.

In similar fashion, duct 738 is mapped or surveyed as it extends toward the axillary nodal basin 726. For example, as before, one or more traverses as represented by the dashed locus 748 are made by moving the probe 20 from the location shown at 20a to that at 20b at the locus 748. When the locale of the sentinel node 734 is reached, a substantial increase in count rate activity will be witnessed at the display 44 and, the procedure then turns to a squelch or threshold based guidance one. In this regard, a threshold base count rate or squelching procedure is carried out at a location adjacent the enhanced count activity region above sentinel node 734, for example at a location represented by the "x" at 750. Following the establishment of the base count rate through either the actuation of switch 27 on probe 20 or the sequential actuation of switches 71 and 70 at console 12, a bracketing procedure again is carried out as described in connection with FIG. 6. Preferably, a transverse traverse over the region of higher activity is made as represented by the dashed line locii 752 and 754. By elevating the threshold base count rate during sequential ones of such traverses through the utilization of switch 52 or a squelch procedure using switch 27, the sentinel node 734 is bracketed until such time as the axis 92 of probe 20 is pointing directly thereat from above it. A small incision then is made and the bracketing procedure continues through the incision until such time as only slight motion of probe 20 is required to carry out a bracketing procedure. As that point in time, the forward face 84 of probe 20 will be in adjacency with sentinel node 734 and the axis thereof of the detector as at 92 will be pointing directly at it. The sentinel node 734 then is removed for evaluation as to the presence or absence of metastasis. Thus, the diagnostic procedure is minimally invasive, other non-affected regional axillary nodes as at 756 not being disturbed.

Figure 26:
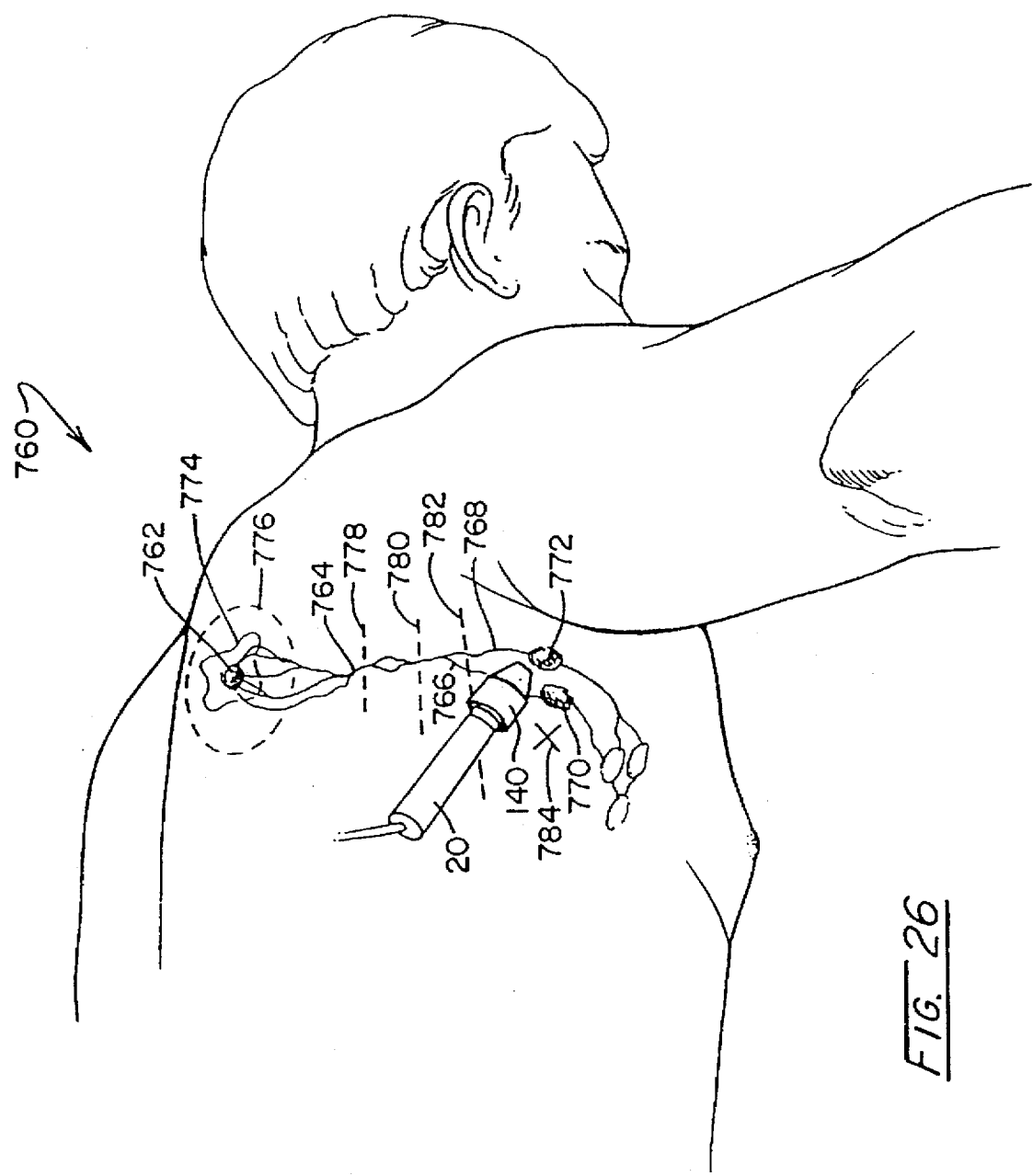
FIG. 26 is a view of the upper torso from the posterior aspect showing a cutaneous melanoma with branch lymph ducting to paired sentinel nodes.

Referring to FIG. 26, an illustration of the upper back of a patient is shown in general at 760 in conjunction with a cutaneous melanoma or lesion 762. The figure illustrates a condition which may occur wherein the lymph duct associated with lesion 762 as at 764 branches as at 766 and 768 such that respectively two sentinel nodes are encountered as at 770 and 772. As before, the lesion 762 is visually identified by the practitioner whereupon a radiopharmaceutical is injected in quadrature to result in a lobed boundary of relatively high count rate activity represented at 774. Following an interval of time permitting migration of the radiopharmaceutical along the duct 764, an initial scan along a locus, for example a circular locus, surrounding and spaced from the site of the neoplastic tissue 762 as well as the boundary 774 is carried out as represented by the dashed circle 776. This procedure, in conjunction with the peak detecting readout 44 will locate that appropriate lymph duct 764 carrying radiopharmaceutical. Accordingly, a sequence of transverse traverses are carried out, for example, along the locii 778, 780, and 782 in the manner described heretofore in conjunction with FIGS. 23–26.

As the mapping traverse, for example at dashed line locus 782 is carried out, two peaks will be observed at the display 44. To differentiate between these peaks, it may be of some value to employ the collimator 140 described above in connection with FIG. 4 and shown in the instant figure with the same numeration in conjunction with probe 20. This typically will provide a differentiation between the two ducts 766 and 768. As the region of the now paired sentinel nodes 770 and 772 is reached, a squelching procedure for example employed by actuation of switch 27 on probe 20 is carried out at the periphery of the enhanced activity around sentinel nodes 770 and 772, for example at the position "x" shown at 784. Using the collimator 140, then transverse traverses can be made at the region of above nodes 770 and 772, and the base count rate adjusting procedure, for example, employing device 48 and particularly switch 54 thereof may be undertaken. As the nodes 770 and 772 are bracketed, the collimator 140 shielding the detector of probe 20 from excessive cross radiation effects, small incisions can be made and the nodes 770 and 772 excised for evaluation with respect to potential metastasis.

Figure 27A:
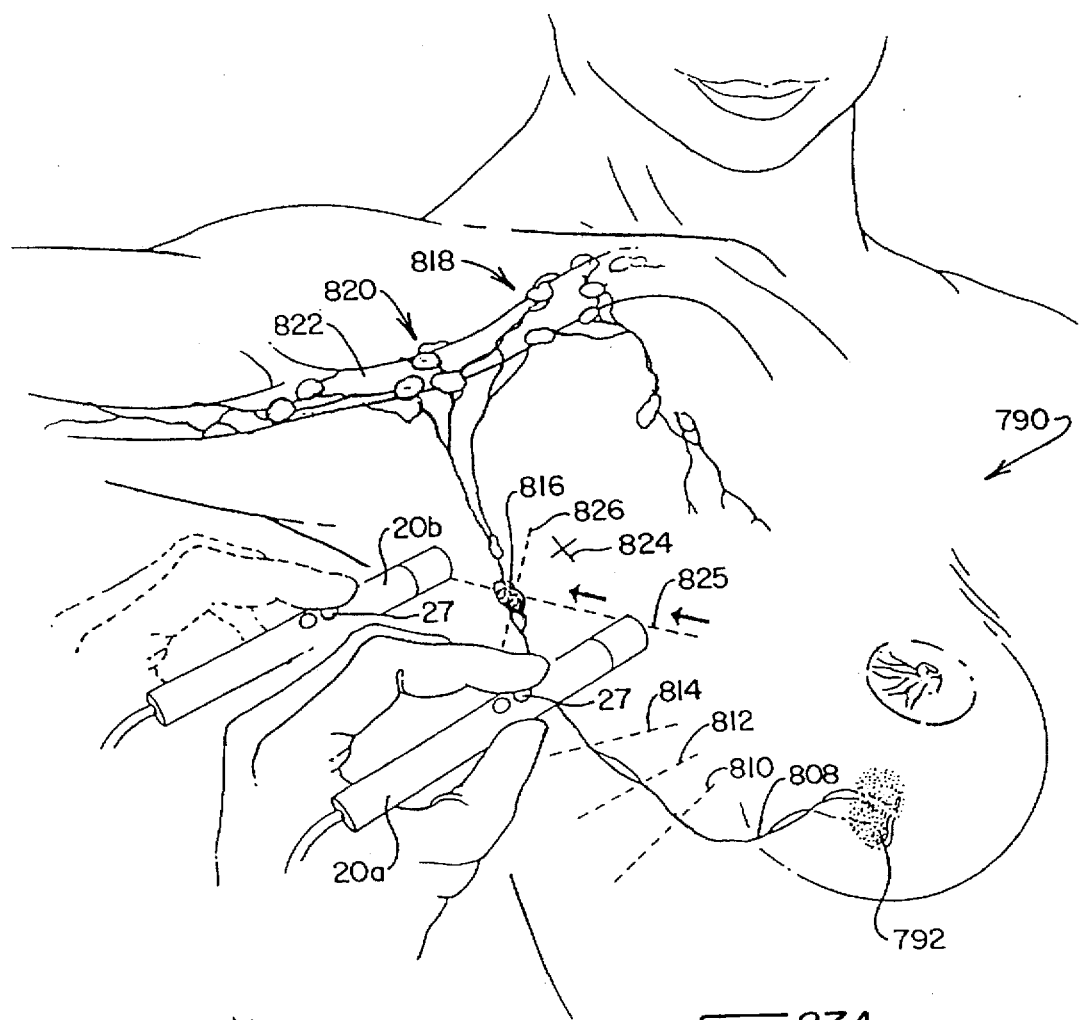
FIG. 27A shows a view of the upper torso from an anterior aspect illustrating lymph duct drainage from a breast tumor.
Figure 27B:
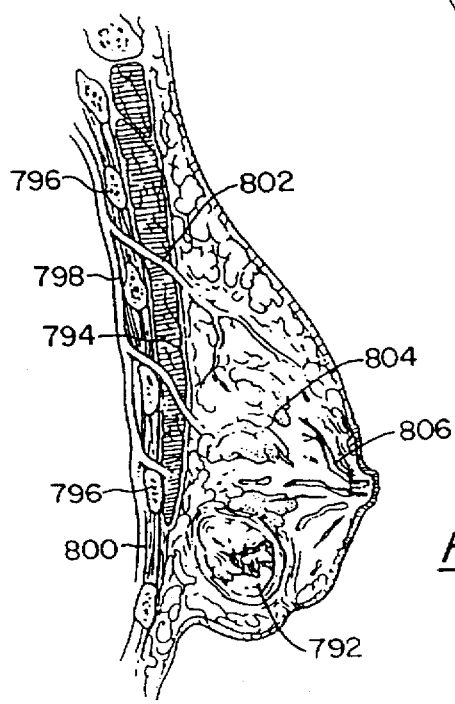
FIG. 27B is a sectional sagital plane view of the breast illustrated in FIG. 27A showing tumor involvement.

The present method also has applicability in locating the sentinel node associated with breast tumor. Looking to FIG. 27A, an illustration of the breast region is represented in general at 790. At this breast region 790 there is depicted an internally disposed tumor 792. Looking additionally to FIG. 27B, the tumor 792 is shown in section, the pectoralis muscles being shown at 794 adjacent ribs 796 and further inwardly disposed inframammary artery 798, intercostal muscle 800, and penetrating or nutrient blood vessels such as shown at 802. The tumor 792 is located within breast tissue represented generally at 804 in conjunction with the ductal system represented generally at 806. By injecting a radiopharmaceutical in the vicinity of tumor 792, the procedure discussed above in connection with melanoma may be carried out to locate a sentinel node. In this regard, the practitioner will know that the lymph duct involved and leading to the sentinel node will be directed toward the axilla. Returning to FIG. 27A, such a lymph duct is shown at 808. Duct 808 may be tracked in the manner described above, for example, by moving the probe 20 traversely with respect thereto while observing readout 44 for peak count rates. Typical traverses or locii for such duct 808 mapping are represented by dashed lines 810, 812, and 814. The sentinel node is illustrated at 816 which will be, for example, present within the regional nodes of the axilla. In this regard, the infraclavicular nodes are shown in general at 818 and the lateral group at 820 in adjacency with the axillary vein 822. As before, as the sentinel node is approached during the mapping of duct 808, a substantial increase in count rate activity will be encountered, whereupon, a squelching or base count rate establishment procedure, for example actuating button switch 27 is carried out at the border of such activity, for example, at the location identified by an "x" at 824. Upon developing a base count rate, then, the region of enhanced activity over sentinel node 816 is transversely traversed, for example, as represented along locii identified at dashed lines 825 and 826. In this regard, the probe is shown initially at 20a with respect to the locus 825 and is seen to pass over the sentinel node 816, the traverse ending at the location of the probe shown at 20b. Bracketing procedures are carried out as described in connection with FIG. 6 above until the sentinel node 816 is identified from above the epidermis. A small incision then is made and the bracketing procedure proceeds using, for example, device 48 and in particular switch 52 thereof. Alternately, resquelching procedures can be carried out using button switch 27. Node 816 then is excised and submitted for evaluation as to cancer involvement. When compared with the conventional surgical protocols of removing essentially all regional lymph nodes at the axilla, the minimally invasive aspect of the present methodology immediately becomes apparent.

Since certain changes may be made in the above described method without departing from the scope of the invention herein involved, it is intended that all matter contained in the description thereof or shown in the accompanying drawings shall be interpreted as illustrative and not in a limiting sense.

We claim:

1. The method for identifying a sentinel lymph node located within a grouping of regional nodes at a lymph drainage basin associated with neoplastic tissue, comprising the steps of:
    (a) identifying the situs of said neoplastic tissue;
    (b) injecting at the situs of said neoplastic tissue a radiopharmaceutical effective for movement with lymph along a lymph duct;
    (c) providing a hand manipulable radiation probe with a detector having a forward surface which is perpendicular to a detector axis, said probe being responsive to photon emissions impinging at said forward surface of said detector to provide probe output signals;
    (d) providing a control system for receiving said probe output signals, said control system providing an energy level validation of said probe output signals and a perceptible output representing a photon count rate of value above a threshold count rate value, said threshold count rate and value being derived in conjunction with a base count rate established by said probe output signals in response to photon emissions from said radiopharmaceutical subsequent to said injection thereof and being actuable to increase said threshold count rate value;
    (e) permitting said radiopharmaceutical to migrate along a lymphatic duct to the situs of a sentinel lymph node following said injection;
    (f) positioning said probe detector forward surface at an initial position at the anticipated region of said situs of said sentinel lymph node and actuating said control system;
    (g) then moving said probe a distance to a next position, and in the presence of a generation of said perceptible output, actuating said control system so as to elevate said threshold count rate value; and
    (h) reiterating step (g) until said movement deriving said perceptible output is of a distance of short extent effective to identify a position of said probe corresponding with a peak rate of said photon emissions impinging at said forward surface of said detector and representing an alignment of said detector axis with said sentinel lymph node.

2. The method of claim 1 in which said step (g) for moving said probe is carried out within a locus of movement wherein said detector axis is substantially retained in parallel relationship with its orientation at said initial position.

3. The method of claim 1 in which said step (g) for moving said probe is carried out within the locus of movement parallel with said detector axis.

4. The method of claim 1 in which an initial said base count rate is derived in response to photon emissions from said radiopharmaceutical at about said initial position.

5. The method of claim 1 in which said threshold count rate initially is derived as said base count rate increased by a select range value, and thereafter as the next previous threshold count rate increased by a select range value.

6. The method of claim 5 in which said select range value is a statistically significant value above said base count rate.

7. The method of claim 5 in which:
    said perceptible output is an audible output; and
    said step (g) actuation of said control system is carried out by manually deriving a said range value selected to adjust said threshold count rate value to a level adequate to terminate said audible output when generated.

8. The method of claim 1 in which said detector forward surface is provided having an area of about 38 square millimeters.

9. The method for identifying a sentinel lymph node located within a grouping of regional nodes at a lymph drainage basin of a patient associated with neoplastic tissue, comprising the steps of:
    (a) identifying the situs of neoplastic tissue;
    (b) injecting through the epidermis of said patient, at the situs of said neoplastic tissue, a radiopharmaceutical effective for movement with lymph along a lymph duct;
    (c) providing a hand manipulable radiation probe with a detector having a forward surface which is perpendicular to a detector axis, said probe being responsive to photon emissions impinging at said forward surface of said detector to provide probe output signals;
    (d) providing a control system for receiving said probe output signals, said control system generating a first visually perceptible graphics output representing a photon count rate corresponding with said probe output signals;
    (e) permitting said radiopharmaceutical to migrate along a lymphatic duct toward the situs of a sentinel lymph node following said injection;
    (f) orienting said probe detector forward surface in a manner defining a scanning surface at a location adjacent said epidermis and within a region adjacent said situs of neoplastic tissue;
    (g) surveying the region of said lymphatic duct with respect to said epidermis by:
        (1) moving said probe outwardly and transversely with respect to said situs of said neoplastic tissue while maintaining said detector forward surface in parallel relationship with said scanning surface;

(2) simultaneously determining peak said photon count rates from said control system first perceptible output;

(3) designating the position of said probe detector axis at said epidermis as extending into adjacency with a portion of said lymphatic duct for each said determined peak photon count;

(4) reiterating steps (1), (2), and (3) until said first perceptible output represents an enhanced photon count rate corresponding with a lymph node contained concentration of said radiopharmaceutical; and (h) locating and isolating said lymph node within the region from which said enhanced photon count rate emanates.

10. The method of claim 9 in which said step (f) includes the steps of:

moving said probe in a locus surrounding and spaced from said situs of neoplastic tissue; and simultaneously determining peak said photon count rates from said control system first perceptible output;

designating the position of said probe detector axis at said epidermis in correspondence with said determined peak outputs as extending into adjacency with a commencing portion of said lymphatic duct.

11. The method of claim 10 in which:

said control system is actuable to provide a second perceptible output representing a photon count rate value above a threshold count rate value derived in conjunction with a base count rate established by said probe output signals generated in response to photon emissions from said radiopharmaceutical;

said step (h) for locating said lymph node includes the steps of:

(1) positioning said probe detector forward surface at the anticipated region of said situs of said sentinel lymph node as determined at step (g)(4) and actuating said control system;

(2) then moving said probe a distance to a next position effective to cause generation of said second perceptible output and actuating said control system so as elevate said threshold count rate value; and (3) reiterating step (2) until said movement deriving said second perceptible output is a distance of short extent effective to derive a position of said probe corresponding with a peak rate of said photon emissions impinging at said forward surface of said detector and representing an alignment of said detector axis with said sentinel lymph node.

12. The method for identifying within a patient, a sentinel lymph node being located within a grouping of regional nodes at a lymph drainage basin associated with neoplastic tissue, comprising the steps of:

(a) identifying the situs of neoplastic tissue;

(b) injecting at the situs of said neoplastic tissue a radiopharmaceutical effective for movement with lymph along a lymph duct;

(c) providing a hand manipulable radiation probe with a detector adjacent a window, said detector having a forward surface which is perpendicular to a detector axis, said probe being responsive to photon emissions impinging at said forward surface of said detector to provide probe output signals;

(d) providing a control system for receiving said probe output signals, said control system providing an energy level validation of said probe output signals and a perceptible output representing a photon count rate of value above a threshold count rate value, said threshold count rate value being derived in conjunction with a base count rate established by said probe output signals in response to photon emissions from said radiopharmaceutical subsequent to said injection thereof and being actuable to increase said threshold count rate value;

(e) permitting said radiopharmaceutical to migrate along a lymphatic duct to the situs of a sentinel lymph node following said injection;

(f) positioning said probe detector forward surface at an initial position at the anticipated region of said situs of said sentinel lymph node and actuating said control system;

(g) then moving said probe transversely along the epidermis of said patient a distance to a next position, and in the presence of a generation of said perceptible output, actuating said control system so as to elevate said threshold count rate value;

(h) reiterating step (g) until said movement deriving said perceptible output is a distance of short extent effective to identify a first position of said probe corresponding with a peak rate of said photon emissions impinging at said forward surface of said detector and representing an alignment of said detector axis with said sentinel lymph node;

(i) forming a surgical opening in said patient at said first position;

(j) then moving said probe window inwardly within said opening to a next position and in the presence of a generation of said next perceptible output, actuating said control system so as to effect a termination of said perceptible output; and (k) reiterating step (j) until said movement deriving said perceptible output is of a limited extent effective to establish a second position of said probe corresponding with a peak rate of said photon emissions impinging at said forward surface of said detector and representing an adjacency of said probe window with said sentinel node.

13. The method of claim 12 in which said perceptible output is an audible output.

14. The method of claim 13 in which said steps (g) and (j) actuations of said control system are carried out by adding count rate values to the next previous threshold count rate at least until said perceptible output terminates.

15. The method of claim 12 in which an initial said base count rate is derived in response to photon emissions from said radiopharmaceutical at about said initial position.

16. The method of claim 12 in which said threshold count rate initially is derived as said base count rate increased by a select range value, and thereafter as the next previous threshold count rate increased by a select range value.

17. The method for identifying a sentinel lymph node located within a grouping of regional nodes at a lymph drainage basin of a patient associated with neoplastic tissue, comprising the steps of:

(a) identifying the situs of a neoplastic tissue;

(b) injecting through the epidermis of said patient, at the situs of said neoplastic tissue, a radiopharmaceutical effective for movement with lymph along a lymph duct;

(c) providing a hand manipulable radiation probe with a detector having a forward surface which is perpendicular to a detector axis, said probe being responsive to photon emissions impinging at said forward surface of said detector to provide probe output signals;

(d) providing a control system for receiving said probe output signals, said control system generating a first visually perceptible graphics output representing a photon count rate corresponding with said probe output signals, said output being a graphic depiction of photon count rate with respect to time provided at a readout;

(e) permitting said radiopharmaceutical to migrate along a lymphatic duct toward the situs of a sentinel lymph node following said injection;

(f) orienting said probe detector forward surface in a manner defining a scanning surface at a location adjacent said epidermis and within a region adjacent said situs of neoplastic tissue, said output being a graphic depiction of photon count rate with respect to time produced at a readout;

(g) surveying the region of said lymphatic duct with respect to said epidermis by:
  (1) moving said probe outwardly and transversely with respect to said situs of neoplastic tissue while maintaining said detector forward surface in parallel relationship with said scanning surface;
  (2) simultaneously determining peak said photon count rates from said control system first perceptible output;
  (3) designating the position of said probe detector axis at said epidermis as extending into adjacency with a portion of said lymphatic duct for each said determined peak photon count;
  (4) reiterating steps (1), (2), and (3) until said first perceptible output represents an enhanced photon count rate corresponding with a lymph node contained concentration of said radiopharmaceutical; and (h) locating and isolating said lymph node within the region from which said enhanced photon count rate emanates.

18. The method of claim 17 in which said graphic time depiction is horizontally scrolled at said readout.

* * * * *